(12) United States Patent
Creasey et al.

(10) Patent No.: US 7,662,774 B2
(45) Date of Patent: *Feb. 16, 2010

(54) METHOD FOR USING LIPOPROTEIN ASSOCIATED COAGULATION INHIBITOR TO TREAT SEPSIS

(75) Inventors: Abla A. Creasey, Piedmont, CA (US); George J. Broze, Ladue, MO (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/891,493

(22) Filed: Jul. 15, 2004

(65) Prior Publication Data

US 2005/0181993 A1    Aug. 18, 2005

Related U.S. Application Data

(63) Continuation of application No. 10/368,000, filed on Feb. 19, 2003, now abandoned, which is a continuation of application No. 09/971,362, filed on Oct. 5, 2001, now abandoned, which is a continuation of application No. 09/521,180, filed on Mar. 8, 2000, now abandoned, which is a continuation of application No. 08/472,761, filed on Jun. 7, 1995, now Pat. No. 6,063,764, which is a continuation-in-part of application No. 08/224,118, filed on Mar. 29, 1994, now abandoned, which is a continuation of application No. 08/020,427, filed on Feb. 22, 1993, now Pat. No. 5,368,148, which is a continuation-in-part of application No. 07/897,135, filed on Jun. 11, 1992, now abandoned, said application No. 08/472,761 and a continuation of application No. 08/253,427, filed on Jun. 2, 1994, now abandoned, is a continuation of application No. 08/004,505, filed on Jan. 13, 1993, now abandoned, which is a continuation-in-part of application No. 07/891,947, filed on Jun. 1, 1992, now abandoned, said application No. 08/472,761 and a continuation-in-part of application No. 08/270,455, filed on Jul. 5, 1994, now abandoned, is a continuation of application No. 07/891,947, filed on Jun. 1, 1992, now abandoned.

(51) Int. Cl.
   *C07K 14/00* (2006.01)
(52) U.S. Cl. .................................. 514/2; 530/350
(58) Field of Classification Search ............ 514/2; 530/350
   See application file for complete search history.

(56) References Cited

U.S. PATENT DOCUMENTS

| 4,179,337 | A | 12/1979 | Davis et al. |
| 4,399,216 | A | 8/1983 | Axel et al. |
| 4,495,285 | A | 1/1985 | Shimizu et al. |
| 4,511,502 | A | 4/1985 | Builder et al. |
| 4,530,787 | A | 7/1985 | Shaked et al. |
| 4,569,790 | A | 2/1986 | Koths et al. |
| 4,572,798 | A | 2/1986 | Koths et al. |
| 4,603,106 | A | 7/1986 | Cerami et al. |
| 4,609,546 | A | 9/1986 | Hiratani |
| 4,620,948 | A | 11/1986 | Builder et al. |
| 4,683,195 | A | 7/1987 | Mullis et al. |
| 4,683,202 | A | 7/1987 | Mullis |
| 4,711,845 | A | 12/1987 | Gelfand et al. |
| 4,748,234 | A | 5/1988 | Dorin et al. |
| 4,766,106 | A | 8/1988 | Katre et al. |
| 4,847,201 | A | 7/1989 | Kawasaki et al. |
| 4,929,700 | A | 5/1990 | Halenbeck et al. |
| 4,966,852 | A | 10/1990 | Wun et al. |
| 5,106,833 | A | 4/1992 | Broze et al. |
| 5,110,730 | A | 5/1992 | Edgington et al. |
| 5,219,994 | A | 6/1993 | Buonassisi et al. |
| 5,223,427 | A | 6/1993 | Edgington et al. |
| 6,063,764 | A | 5/2000 | Creasey |

FOREIGN PATENT DOCUMENTS

| EP | 268110 | 5/1988 |
| EP | 270799 | 6/1988 |
| EP | 318451 | 5/1989 |
| EP | 473564 | 3/1992 |
| WO | WO 85/04899 | 11/1985 |
| WO | 90/08158 | 7/1990 |
| WO | 91/02753 | 3/1991 |
| WO | WO 91/19514 | 12/1991 |
| WO | 92/07584 | 5/1992 |
| WO | WO 93/25230 | 12/1993 |

(Continued)

OTHER PUBLICATIONS

Record, Kenneth E., Chapter 87/Gram-Negative Sepsis and Septic Shock, Pharmacotherapy, A Pathophysiologic Approach, Editors, DiPiro, New York, (1989), pp. 1258-1265.*

Stedman's Medical Dictionary, 25th Edition, Williams & Wilkin's, Baltimore, (1990), p. 1268.*

Ameri et al., "Expression of Tissue Factor Pathway Inhibitor by Cultured Endothelial Cells in Response to Inflammatory Mediators", *Blood*, 79:3219-26 (1992).

(Continued)

*Primary Examiner*—Karen Cochrane Carlson
(74) *Attorney, Agent, or Firm*—Banner & Witcoff, Ltd.

(57) ABSTRACT

A method for prophylactically or therapeutically treating sepsis or septic shock is described, wherein an inhibitor to tissue factor is administered to septic patients. Additionally, a method for treating inflammation is described wherein the inhibitor is administered to patients. This inhibitor is termed lipoprotein associated coagulation inhibitor, or commonly LACI. It is 38 kD and has 276 amino acids. LACI has now been shown to be useful for the treatment of sepsis, septic shock and inflammation.

7 Claims, 5 Drawing Sheets

OTHER PUBLICATIONS

Bailey et al, "Methylmercury as a Reversible Denaturing Agent for Agarose Gel Electrophoresis", *Anal. Bioch.*, 70:75 (1976).

Bajaj et al., "Cultured normal human hepatocytes do not synthesize lipoprotein-associated coagulation inhibitor: Evidence that endothelium is the principal site of its synthesis", *PNAS (USA)*, 87:8869-73 (1990).

Bajaj et al., "Inhibitor of the Factor VIIa-Tissue Factor Complex is Reduced in Patients with Disseminated Intravascular Coagulation but Not in Patients with Severe Hepatocellular Disease", *J. Clin. Invest.*, 79:1874 (1987).

Bevilacqua et al., "Recombinant tumor necrosis factor induces procoagulant activity in cultured human vascular endothelium: Characterization and comparison with the actions of interleukin 1 ", *PNAS (USA)*, 83:4533-37 (1986).

Bolivar et al., "Construction and Characterization of New Cloning Vehicles", *Gene*, 2:95 (1977).

Bone et al., "Definitions for Sepsis and Organ Failure and Guidelines for the Use of Innovative Therapies in Sepsis", *Chest*, 101:1644-1655 (1992).

Broach, "Construction of High Copy Yeast Vectors Using 2-µm Circle Sequences", *Meth. Enzymol.*, 101:307 (1983).

Broach, "Transformation in Yeast: Development of a Hybrid Cloning Vector and Isolation of the *CAN1* Gene", *Gene*, 8:121 (1979).

Broze et al., "Regulation of Coagulation by a Multivalent Kunitz-Type Inhibitor", *Biochemistry*, 29: 7539-46 (1990).

Broze et al., "The Lipoprotein-Associated Coagulation Inhibitor That Inhibits the Factor VII-Tissue Factor Complex Also Inhibits Factor Xa: Insight Into Its Possible Mechanism of Action", *Blood*, 71:335-343 (1988).

Broze et al., "Isolation of the tissue factor inhibitor produced by HepG2 bepatoma cells", *PNAS (USA)*, 84:1886-1890 (1987).

Clarke et al., "Selection Procedure for Isolation of Centromere DNAs from *Saccharomyces cerevisiae* ", *Meth. Enzymol.*, 101:300 (1983).

Clewell et al., "Nature of Col E, Plasmid Replication in *Escherichia coli* in the Presence of Chloramphenicol", *J. Bacteriol.*, 110.-667 (1972).

Clewell et al, "Supercoiled Circular DNA-Protein Complex in *Escherichia Coli*: Purification and Induced Conversion to an Open Circular DNA Form", *PNAS (USA)*. 62:1159 (1969).

Cohen et al, "Nonchromosomal Antibiotic Resistance in Bacteria: Genetic Transformation of *Escherichia coli* by R-Factor DNA", *PNAS (USA)*. 69:2110 (1972).

Colucci et al., "Cultured Human Endothelial Cells Generate Tissue Factor in Response to Endotoxin", *J. Clin. Invest.*, 71:1893-96 (1983).

Corrigan, "Heparin therapy in bacterial septicemia", *J. Pediatrics*. 91:695 (1977).

Creasey et al., "Tissue Factor Pathway Inhibitor Reduces Mortality from *Escherichia coil* Septic Shock", *J. Clin. Invest.*, 91:2850-56 (1993).

Creasey et al., "Endotoxin and Cytokine Profile in Plasma of Baboons Challenged With Lethal and Sublethal *Escherichia coil*", *Circ. Shock*, 33:84-91 (1991).

Cross et al., "Choice of Bacteria in Animal Models of Sepsis", *Infect. Immun.*, 61:2741-47 (1993).

Day et al., "Recombinant Lipoprotein-Associated Coagulation Inhibitor Inhibits Tissue Thromboplastin-Induced Intravascular Coagulation in the Rabbit", *Blood*, 76:1538-1545 (1990).

Depicker et al, "Nopaline Synthase: Transcript Mapping and DNA Sequence", *J. Mol. Appl. Gen.* 1:561 (1982).

Expanded Antril data fails to impress investors, Biotechnology Business News, Mar. 26, 1993.

Fiers et al., "Complete nucleotide sequence of SV40 DNA", *Nature*, 273:113 (1978).

Fink et al, "Laboratory Models of Sepsis and Septic Shock", *J. Surgical Res.*, 49:186-196(1990).

Fischer et al., "Interleukin-I Receptor Blockade Improves Survival and Hemodynamic Performance in *Escherichia coil* Septic Shock, But Falls to Alter Host Responses to Sublethal Endotoxemia", *J. Clin. Invest.*, 89:1551-1557 (1992).

Fitzer-Schiller, "Synergen Stock Falls Again on Delay in Marketing Application", The Reuter Business Report, Mar. 23, 1993.

Goeddel et al., "Synthesis of human fibroblast interferon by *E. coil*", *Nucl. Acids Res.*. 8:4057 (1980).

Graham et al., "A New Technique for the Asszy of Infectivity of Human Adenovirus 5 DNA", *Virology*, 52:456 (1973).

Hess et al., "Cooperation of Glycolytic Enzymes", *J. Adv. Enzyme Reg.*, 7:149 (1968).

Hinshaw et al., "Detection of the 'Hyperdynamic State' of Sepsis in the Baboon during Lethal *E. coil* Infusion", *J. Trauma*, 23:361-365 (1983).

Hinshaw et al, "Survival of Primates in $LD_{100}$ Septic Shock Following Therapy with Antibody to Tumor Necrosis Factor (TNFα)", *Circulatory Shock*, 30:279-292 (1990).

Hitzeman et al., "Isolation and Characterization of the Yeast 3-Phosphoglycerokinase Gene (PGk) by an Immunological Screening Technique", *J. Biol. Chem.*, 255:12073 (1980).

Holland et al., "The Primary Structures of Two Yeast Enolase Genes", *J. Biol. Chem.*, 256:1385 (1981).

Holland et al., "Isolation and Identification of Yeast Messenger Ribonucleic Acids Coding for Enolase, Glyceraldehyde-3-phosphate Dehydrogenase, and Phosphogiycerate Kinase", *Biochemisary*, 17:4900 (1978).

Hsiao et al., "High-frequency transformation of yeast by plasmids containing the cloned yeast ARG4 gene", *PNAS (USA)* 76:3829 (1979).

Knauf et al., "Relationship of Effective Molecular Size to Systemic Clearance in Rats of Recombinant Interleukin-2 Chemically Modified with Water-Soluble Polymers", *J. Biol. Chem.*, 263:15064 (1988).

Lyberg et al., "Cellular cooperation in endothelial cell thromboplastin synthesis", *Br. J. Haematol.*, 53:85-95 (1983).

Matteucci et al., "Synthesis of Deoxyoligonucleotides on a Polymer Support", *J. Am. Chem. Soc.*, 103:3185 (1981).

Martin et al., Natural History in the 1980's, Abstract No. 317, ICAAC Meeting, Dallas (1989).

Maxam et al., "Sequencing End-Labeled DNA with Base-Specific Chemical Cleavages", *Meth. Enzymol.*, 65:499 (1980).

Messing et al., "A system for shotgun DNA sequencing", *Nucl. Acids Res.*, 9:309 (1981).

Muller-Berghaus, "Pathophysiologic and Biochemical Events in Disseminated Intravascular Coagulation: Dysregulation of Procoagulant and Anticoagulant Pahtways", *Sem. Thromb. Haemost.*, 15:58-87 (1989).

Narwroth et al, "Interleukin 1 induces endothelial cell procoagulant while suppressing cell-surface anticoagulant activity", *PNAS (USA)*, 83:3460-64 (1986).

Nemerson, "Tissue Factor and Hemostasis", *Blood*, 71:1-8 (1988).

Novotny et al., "Purification and Properties of Heparin-Releasable Lipoprotein-Associated Coagulation Inhibitor", *Blood*, 78:394-400 (1991) .

Novotny et al., "Purification and Characterization of the Lipoprotein-Associated Coagulation Inhibitor from Human Plasma", *J. Biol. Chem.*, 264:18832-18837 (1989).

Osterud et al., "Increased Tissue Thromboplastin Activity in Monocytes of Patients with Meningococcal Infection: Related to an Unfavourable Prognosis", *Thrombosis Haemost.*, 49:5-7 (1983) .

Pedersen et al., "Recombinant Human Extrinsic Pathway Inhibitor", *J. Biol. Chem.*, 265:16786-16793 (1990).

Quezado et al., "Therapies Directed Against Endotoxin—Has the Time Come?", *Western J. of Med.*, 158:424-425 (1993).

Rapaport, Inhibition of Factor VIIa/Tissue Factor-Induced Blood Coagulation: With Particular Emphasis Upon a Factor Xa-Dependent Inhibitory Mechanism, *Blood*, 73: 359-365 (1989).

Rapaport, "The Extrinsic Pathway Inhibitor: A Regulator of Tissue Factor-Dependent Blood Coagulation", *Thrombosis Haemost.*, 66:6-15 (1991).

Rhein, "Another sepsis drug down—Immunex" TNF receptor, Biotechnology Newswatch, Monday, Oct. 4, 1993, pp. 1,3.

Rivers et al., "The Endotoxin-induced Coagulant Activity of Human Monocytes", *Br. J. Haemotol.*, 30:311-316 (1975).

Sandset et al., "Coagulation inhibitor levels in pneumonia and stroke: changes due to consumption and acute phase reaction" *J. Internal Med.* 225:311 (1989).

Sandset et al., "Depletion of extrinsic pathway inhibitor (EPI) sensitizes rabbits to disseminated intravascular coagulation induced with tissue factor: Evidence supporting a physiologic role for EPI as a natural anticoagulant", *PNAS (USA)*, 88:708-712 (1991).

Sandset et al., "Extrinsic Pathway Inhibitor in Postoperative/Post-traumatic Septicemia: Increased Levels in Fatal Cases", *Haemostasis*, 19:189 (1989).

Sandset et al., Heparin Induces Release of Extrinsic Coagulation Pathway Inhibitor (EPI) *Thrombosis Res.*, 50:808-813 (1988).

Sanger et al., "DNA sequencing with chain-terminating inhibitors", *PNAS (USA)*, 74:5463 (1977).

Shegal et al., "Heterogeneity of poly(I).poly(c) induced human fibroblast interferon mRNA species", *Nature*, 288:95 (1980).

Shaw et al., "A general method for the transfer of cloned genes to plant cells", *Gene*, 23:315 (1983).

Shimatake et al., "Purified λ regulatory protein cII positively activates promoters for lysogenic development", *Nature*, 292:128 (1981).

Stinchcomb et al., "Isolation and characterization of a yeast chromosomal replicator", *Nature*, 282:39 (1979).

Taylor et al, "DEGR-Factor Xa Blocks Disseminated. Intravascular Coagulation Initiated by *Escherichia coli* Without Preventing Shock or Organ Damage", *Blood*, 78:364-368 (1991) .

Taylor et al., "Lethal *E. Coil* Septic Shock is Prevented by Blocking Tissue Factor With Monoclonal Antibody", *Circulatory Shock*, 33:127-134 (1991).

Taylor, "Baboon Model of *E. Coil* Sepsis: Summary of Staging, Mechanism, and Diagnostic Markers", in *Molecular Aspects of Inflammation*, 42. Colloquium Mosbach,-Springer-Verlag Berlin, pp. 277-288 (1991).

Tschempe et al, "Sequence of a yeast DNA fragment containing a chromosomal replicator and the TRP1 gene", *Gene*, 10:157 (1980).

Van Solingen et al., "Fusion of Yeast Spheroplasts", *J. Bact.*, 130:946 (1977).

Warr et al., "Disseminated Intravascular Coagulation in Rabbits Induced by Administration of Endotoxin or Tissue Factor_Effect of Anti-Tissue Factor Antibodies and Measurement of Plasma Extrinsic Pathway Inhibitor Activity," *Blood*, 75:1481-1489 (1990) .

Wherry et al., "Monoclonal Antibody to Human Tumor Necrosis Factor (TNF Mab): Multi-eenter Efficacy and Safety Study in Patients with the Sepsis Syndrome", at 33rd Interscience Conference on Antimicrobial Agents and Chemotherapy (ICAAC), New Orleans, Louisiana, Oct. 17-20, 1993.

Wun et al., "Cloning and Characterization of a cDNA Coding for the Lipoprotein-associated Coagulation Inhibitor Shows That It Consists of Three Tandem Kunitz-type Inhibitory Domains", *J. Biological Chemistry*, 263: 6001-6004 (1988).

Wun et al, "Immunoaffinity Purification and Characterization of Lipoprotein-associated Coagulation Inhibitors from Hep G2 Hepatoma, Chang Liver, and SK Hepatoma Cells," *J. Biol. Chem.*, 265:16096-16101 (1990).

Wun et al., "Comparison of Recombinant Tissue Factor Pathway Inhibitors Expressed in Human SK Hepatoma, Mouse C127, Baby Hamster Kidney, and Chinese Hamster Ovary Cells", *Thrombosis Haemostasis*, 68:54-59 (1992).

Zinsser, *MicroBiology*,17th ed., W. Joklik et al., eds., pp. 235-277 (1980).

U.S. Appl. No. 10/141,918, filed May 10, 2002, Creasey.

Valentin et al., "Simultaneous presence of tissue factor pathway inhibitor (TFPI) and low molecular weight heparin has a synergistic effect . . . ", *Blood Coagul. Fibrinolysis*, 2:629-635 (1991).

Nordfang et al., *Thrombosis Haemost.*, F.K. Schattauer Verlagsgesellschaft mbH (Stuttgart) 55:464-467.

Nordfang et al., *Biochemistry*, 30:10371-10376(1991).

Lindhout et al., *Blood*, 79:2909-2916(1992).

Callander et al., *J. Biol. Chem.*, 267:876-882 (1992).

Petersen et al., *Thrombosis Haemost.*, F.K. Schattauer Verlagsgesellschaft mbH (Stutigart) 67:537-541(1992).

Kristensen et al., *Thrombosis Haemost*, F.K. Schattauer Verlagsgesellschaft mbH (Stuttgart) 68:310-314 (1992).

Valentin et al., *Blood Coagul Fibrinolysis*, 3:221-222 (1992).

Girard et al., *Thromb. Res.*, 55:37-50 (1989).

Girard et al., *Nature*, 338:518-520 (1989).

Haskel et al., *Circulation*, 84:821-827(1991).

Kunkel et al., *Proc. Nat. Acad. Sci. USA*, 82.488-492 (1985).

Olines et al., *J. Biol. Chem.*, 264:16973-16976(1989).

Maniatis et al., *Molecular Cloning: A Laboratory Manual*, Cold Spring Harbor, N.Y. (1982).

Obukowicz et al., *Biochemistry*, 29:9737-9745 (1990).

Ostergaard et al., *Haemostasis*, 23:221-222 (1993).

Holst et al., *Haemostasis*, 23:112-117(1993).

Hamamoto et al., *J. Biol. Chem.*, 268:8704-8710(1993).

Corrigan et al., "Heparin Therapy in Septicemia with Disseminated Intravascular Coagulation. Effect on Mortality and on Correction of Hemostatic Defects", *N. Engl. J. Med.*, 283:778-712 (1970).

Lasch et al., "Heparin Therapy of Diffuse Intravascular Coagulation (DIC)", *Thrombos. Diathes. Haemorrh.*,33:105 (1974).

Straub, "A Case Against Heparin Therapy of Intravascular Coagulation", *Thrombos. Diathes. Haemorrh.*, 33:107 (1974).

Brozna, "Cellular Regulation of Tissue Factor", *Blood Coagul. Fibrinolysis*, 1:415-426(1990).

Sandset et al., "Immamodepletion of Extrinsic Pathway Inhibitor Sensitizes Rabbits to Endotoxin-Induced Intarvascular Coagulation and the Generalized Shwartzman Reaction", *Blood*, 78:1496-1502(1991).

Warr et al., "Human Plasma Extrinsic Pathway Inhibitor Activity:II. Plasma Levels in Disseminaud Intravascular Coagulation and Hepatoecllular Disease", *Blood*, 74:994-998 (1989).

Abraham et al., "Efficacy and Safety of Tifacogin (Recombinant Tissue Factor Pathway Inhibitor) in Sever Sepsis; A Randomized Controlled Trial", JAMA, Jul. 9, 2003, pp. 238-247, vol. 290, No. 2, American Medical Association.

Angus et al., "Unraveling Severe Sepsis; Why did Optimist Fail and What's Next?," JAMA, Jul. 9, 2003, pp. 256-258, vol. 290, No. 2, American Medical Association.

* cited by examiner

METHOD FOR USING LIPOPROTEIN ASSOCIATED COAGULATION INHIBITOR TO TREAT SEPSIS

CROSS-REFERENCE TO RELATED APPLICATIONS

This application is a continuation of U.S. Ser. No. 10/368,000, filed Feb. 19, 2003 (abandoned), which is a continuation of U.S. Ser. No. 09/971,362, filed Oct. 5, 2001 (abandoned), which is a continuation of U.S. Ser. No. 09/521,180, filed Mar. 8, 2000 (abandoned), which is a continuation of Ser. No. 08/472,761, filed Jun. 7, 1995 (now U.S. Pat. No. 6,063,764), which is a continuation-in-part of U.S. Ser. No. 08/224,118, filed Mar. 29, 1994 (abandoned), which is a continuation of Ser. No. 08/020,472 filed Feb. 22, 1993 now U.S. Pat. No. 5,368,148, which is a continuation-in-part of Ser. No. 07/897,135, filed Jun. 11, 1992 (abandoned). U.S. Ser. No. 08/472,761, filed Jun. 7, 1995 is also a continuation-in-part of Ser. No. 08/253,427, filed Jun. 2, 1994 (abandoned), which is a continuation of Ser. No. 08/004,505 filed Jan. 13, 1993 (abandoned), which is a continuation-in-part of Ser. No. 07/891,947, filed Jun. 1, 1992 (abandoned). U.S. Ser. No. 08/472,761, filed Jun. 7, 1995 is also a continuation-in-part of Ser. No. 08/270,455 filed Jul. 5, 1994 (abandoned), which is a continuation of Ser. No. 07/891,947, filed Jun. 1, 1992 (abandoned).

FIELD OF THE INVENTION

The present invention is a method for prophylactically and therapeutically treating acute and chronic inflammation, sepsis and septic shock. More specifically, it comprises administering a therapeutically effective amount of a specific protein to attenuate physiological pathways associated with septic shock.

BACKGROUND OF THE INVENTION

Lipoprotein-associated coagulation inhibitor (LACI) is a protein inhibitor present in mammalian blood plasma. LACI is also known as tissue factor (TF) inhibitor, tissue thromboplastin (Factor III) inhibitor, extrinsic pathway inhibitor (EPI) and tissue factor pathway inhibitor (TFPI).

Blood coagulation is the conversion of fluid blood to a solid gel or clot. The main event is the conversion of soluble fibrinogen to insoluble strands of fibrin, although fibrin itself forms only 0.15% of the total blood clot. This conversion is the last step in a complex enzyme cascade. The components (factors) are present as zymogens, inactive precursors of proteolytic enzymes, which are converted into active enzymes by proteolytic cleavage at specific sites. Activation of a small amount of one factor catalyses the formation of larger amounts of the next, and so on, giving an amplification which results in an extremely rapid formation of fibrin.

The coagulation cascade which occurs in mammalian blood is divided by in vitro methods into an intrinsic system (all factors present in the blood) and an extrinsic system which depends on the addition of thromboplastin. The intrinsic pathway commences when the first zymogen, factor XII or 'Hageman Factor', adheres to a negatively charged surface and in the presence of high molecular weight kininogen and prekallikrein, becomes an active enzyme, designated XIIa. The activating surface may be collagen which is exposed by tissue injury. Factor XIIa activates factor XI to give XIa, factor XIa activates factor IX to IXa and this, in the presence of calcium ions, a negatively charged phospholipid surface and factor VIIIa, activates factor X. The negatively charged phospholipid surface is provided by platelets and in vivo this serves to localize the process of coagulation to sites of platelet deposition. Factor Xa, in the presence of calcium ions, a platelet-derived negatively charged phospholinid surface and a binding protein, factor V, activates prothrombin to give thrombin (IIa)—the main enzyme of the cascade. Thrombin, acting on gly-arg bonds, removes small fibrinopeptides from the N-terminal regions of the large dimeric fibrinogen molecules, enabling them to polymerize to form strands of fibrin. Thrombin also activates the fibrin stabilizing factor, factor XIII, to give XIIIa, a fibrinoligase, which, in the presence of calcium ions strengthens the fibrin-to-fibrin links with intermolecular γ-glutamyl-ε-lysine bridges. In addition, thrombin acts directly on platelets to cause aggregation, and release of subcellular constituents and arachidonic acid. A further function of thrombin is to activate the coagulation inhibitor, protein C. Factors XIIa, XIa, IXa, Xa, and thrombin are all serine proteases.

The extrinsic pathway in vivo is initiated by a substance generated by, or exposed by, tissue damage and termed 'tissue factor', interacting with Factor VII in the presence of calcium ions and phospholipid to activate factors X and IX, after which the sequence proceeds as already described. The identity of TF is known. There is evidence that tissue factor occurs in the plasma membranes of perturbed endothelial cells of blood vessels and also in atheromatous plaques.

The two pathways described are not entirely separate because both factor IXa and factor XIIa in the intrinsic pathway may activate factor VII in the extrinsic pathway. There are, in addition, various feedback loops between other factors, which enhance reaction rates. For example, thrombin (IIa) enhances the activation of both factor V and factor VIII.

Sepsis and its sequela septic shock remain among the most dreaded complications after surgery and in critically ill patients. The Center for Disease Control ranks septicemia as the 13th leading cause of death in the United States (see MMWR, 1987, 39:31 and *US Dept. of Health and Human Services*, 37:7, 1989), and the 10th leading cause of death among elderly Americans (see MMWR, 1987, 39:777). The incidence of these disorders is increasing, and mortality remains high. Estimates of the total cost of caring for patients with septicemia range from $5 billion to $10 billion annually (see MMWR, 1987, 39:31). Death can occur in 40% to 60% of the patients. This percentage has not seen any improvement over the past 20 years. The incidence of blood borne gram-positive and gram-negative infections that can lead to septic shock occur approximately equally.

Sepsis is a toxic condition resulting from the spread of bacteria, or their products (collectively referred to herein as bacterial endotoxins) from a focus of infection. Septicemia is a form of sepsis, and more particularly is a toxic condition resulting from invasion of the blood stream by bacterial endotoxins from a focus of infection. Sepsis can cause shock in many ways, some related to the primary focus of infection and some related to the systemic effects of the bacterial endotoxins. For example, in septaemia, bacterial endotoxins, along with other cell-derived materials, such as IL-1, IL-6 and TNF, activate the coagulation system and initiate platelet aggregation. The process leads to blood clotting, a drop in blood pressure and finally kidney, heart and lung failure.

Septic shock is characterized by inadequate tissue perfusion, leading to insufficient oxygen supply to tissues, hypotension and oliguria. Septic shock occurs because bacterial products, principally LPS, react with cell membranes and components of the coagulation, complement, fibrinolytic, bradykinin and immune systems to activate coagulation, injure cells and alter blood flow, especially in the microvasculature. Microorganisms frequently activate the classic complement pathway, and endotoxin activates the alternate pathway. Complement activation, leukotriene generation and the direct effects of endotoxin on neutrophils lead to accumulation of these inflammatory cells in the lungs, release of the enzymes and production of toxic oxygen radicals which damage the pulmonary endothelium and initiate the acute respiratory distress syndrome (ARDS). ARDS is a major cause of death in patients with septic shock and is characterized by pulmonary congestion, granulocyte aggregation, hemorrhage and capillary thrombi.

Activation of the coagulation cascade by bacterial endotoxins introduced directly into the bloodstream can result in extensive fibrin deposition on arterial surfaces with depletion of fibrinogen, prothrombin, factors V and VIII, and platelets. In addition, the fibrinolytic system is stimulated, resulting in further formation of fibrin degradation products. Disseminated intravascular coagulation (DIC) is a complex coagulation disorder resulting from widespread activation of the clotting mechanism or coagulation cascade which, in turn, results from septicemia. Essentially, the process represents conversion of plasma to serum within the circulation system. Such process represents one of the most serious acquired coagulation disorders. Some common complications of disseminated intravascular coagulation are severe clinical bleeding, thrombosis, tissue ischaemia and necrosis, hemolysis and organ failure.

At the same time, as coagulation is apparently initiated by endotoxin, countervening mechanisms also appear to be activated by clotting, namely activation of the fibrinolytic system. Activated Factor XII converts plasminogen pro-activator to plasminogen activator which subsequently converts plasminogen to plasmin thereby mediating clot lysis. The activation of plasma fibrinolytic systems may therefore also contribute to bleeding tendencies.

Endotoxemia is associated with an increase in the circulating levels of tissue plasminogen activator inhibitor (PAI). This inhibitor rapidly inactivates tissue plasminogen activator (TPA), thereby hindering its ability to promote fibrinolysis through activation of plasminogen to plasmin. Impairment of fibrinolysis may cause fibrin deposition in blood vessels, thus contributing to the disseminated intravascular coagulation associated with septic shock.

Disseminated intravascular coagulation (DIC) is a coagulopathic disorder that occurs in response to invading microorganisms characterized by widespread deposition of fibrin in small vessels. The initiating cause of DIC appears to be the release of thromboplastin (tissue factor) into the circulation. During this process, there is a reduction in fibrinogen and platelets, and a rise in fibrin split products resulting in fibrin deposition in blood vessels. The sequence of events that occur during DIC are described in FIG. 1. The patients either suffer from thrombosis or hemorrhage depending on the extent of exhaustion of the coagulation protease inhibitors during the disease process. Part of the regulation of the coagulation cascade depends on the rate of blood flow. When flow is decreased, as it is in DIC and sepsis, the problems are magnified. DIC (clinically mild to severe form) is thought to occur with high frequency in septic shock patients and several other syndromes such as head trauma and burns, obstetric complications, transfusion reactions, and cancer. A recent abstract by Xoma Corporation indicates that DIC was present on entry in 24% of septic patients (Martin et al., 1989, *Natural History in the 1980s*, Abstract No. 317, ICAAC Meeting, Dallas). Furthermore, the abstract describes that DIC and acute respiratory distress syndrome were the variables most predictive of death by day 7 (risk ratios 4 and 2.3). The cascade of events that lead to release of tissue factor into circulation and sepsis is very complex. Various cytokines are released from activated monocytes, endothelial cells and others; these cytokines include tumor necrosis factor (TNF), interleukin 1 (IL-1) (which are known to up-regulate tissue factor expression), interleukin 6 (IL-6), gamma interferon (IFN-γ), interleukin 8 (IL-8), and others. The complement cascade is also activated as demonstrated by the rise in C3a and C5a levels in plasma of septic patients. Consequently, an agent that will treat coagulation without affecting the expression of tissue factor or its activity will not necessarily be effective to treat sepsis.

There are currently no satisfactory interventions for the prevention or treatment of sepsis or DIC. Heparin is the most commonly used anticoagulant in DIC. However, it has been controversial because it can induce bleeding and worsen the patient's condition. See, for example, Corrigan et al., "Heparin Therapy in Septacemia with Disseminated Intravascular Coagulation. Effect on Mortality and on Correction of Hemostatic Defects", *N. Engl. J. Med.*, 283:778-782 (1970); Iasch et al., Heparin Therapy of Diffuse Intravascular Coagulation (DIC)", *Thrombos. Diathes. Haemorrh.*, 33:105 (1974); Straub, "A Case Against Heparin Therapy of Intravascular Coagulation", *Thrombos. Diathes. Haemorrh.*, 33:107 (1974).

Other attempts to treat sepsis using an anticoagulant have also been difficult. As shown in Taylor et al., 1991, *Blood*, 78:364-368, warfarin and heparin are mentioned as two anticoagulants that are used to treat DIC in sepsis, but neither are the ideal drugs. Additionally, Taylor et al. show that a new drug DEGR-Xa, a factor Xa antagonist, can inhibit DIC, however, this drug failed to block the lethal effects of sepsis. Consequently, it is evident that an agent which may interrupt the coagulation pathway is not necessarily effective as an inhibitor of septic shock. Therefore, there is a need in the art for a composition that will inhibit the lethal effects of sepsis.

SUMMARY OF THE INVENTION

The present invention is a method for prophylactically and therapeutically treating syndromes associated with acute or chronic inflammation where activation of Factor VII, Xa and tissue factor expression are involved, such as sepsis and septic shock, whether accompanied by DIC or not. The method comprises administering an effective amount of lipoprotein associated coagulation inhibitor (LACI). Additionally, the present invention is a method, comprising administering LACI, to treat a disease state in which TNF, IL-1, IL-6 or other cytokines up-regulate tissue factor. Specifically, these disease states include acute or chronic inflammation. Preferably, LACI is intravenously administered at a dose between 1 μg/kg and 20 mg/kg, more preferably between 20 μg/kg and 10 mg/kg, most preferably between 1 and 7 mg/kg. LACI is preferably administered with an additional agent to treat sepsis and septic shock, such as an antibiotic.

Among other things, it has been surprisingly discovered that a compound known for its anti-coagulant properties, can also attenuate the immune response and serve as a treatment for sepsis and septic shock. This was surprising in view of the findings of Warr et al., 1990, *Blood*, 75:1481-1489 and Taylor et al., 1991, *Blood*, 78:364-368.

BRIEF DESCRIPTION OF THE DRAWINGS AND TABLE

FIG. 1 shows the complex pathways involved in Sepsis and septic shock. The intrinsic and extrinsic pathways are included. Signs of microvascular thrombosis include: (1) neurologic: multifocal, delerium, coma; (2) skin: focal ischemia, superficial gangrene; (3) renal: oliguria, azotemia, cortical necrosis; (4) pulmonary; acute respiratory distress syndrome; and (5) gastrointestinal: acute ulceration. Signs of hemorrhagic diathesis include: (1) neurologic: intracerebral bleeding; (2) skin: petechiae, ecchymoses, venepuncture oozing; (3) renal; hematuria; (4) mucous membranes: epistaxis, gingival oozing; and (5) gastrointestinal: massive bleeding.

Figure 5A:
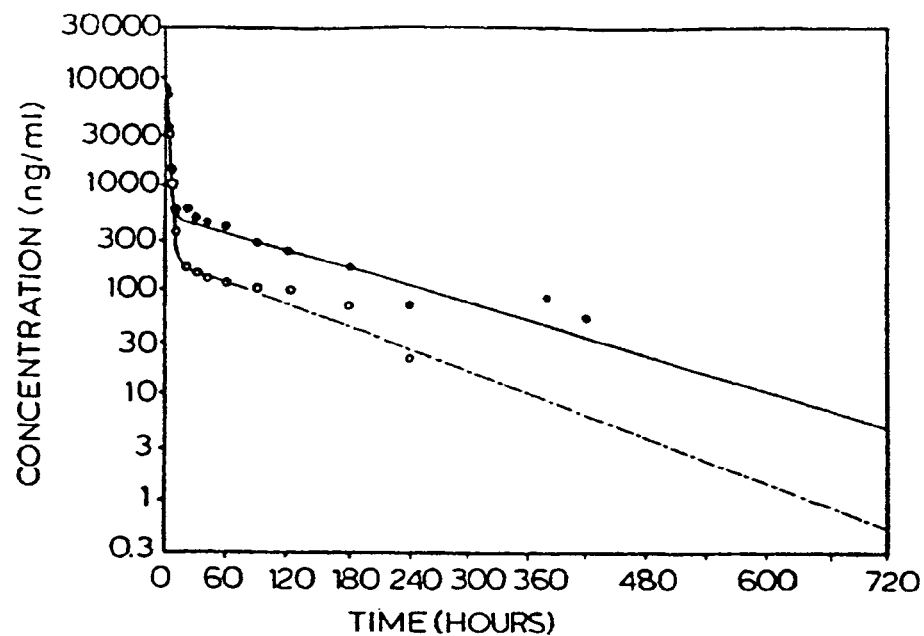
Figure 5B:
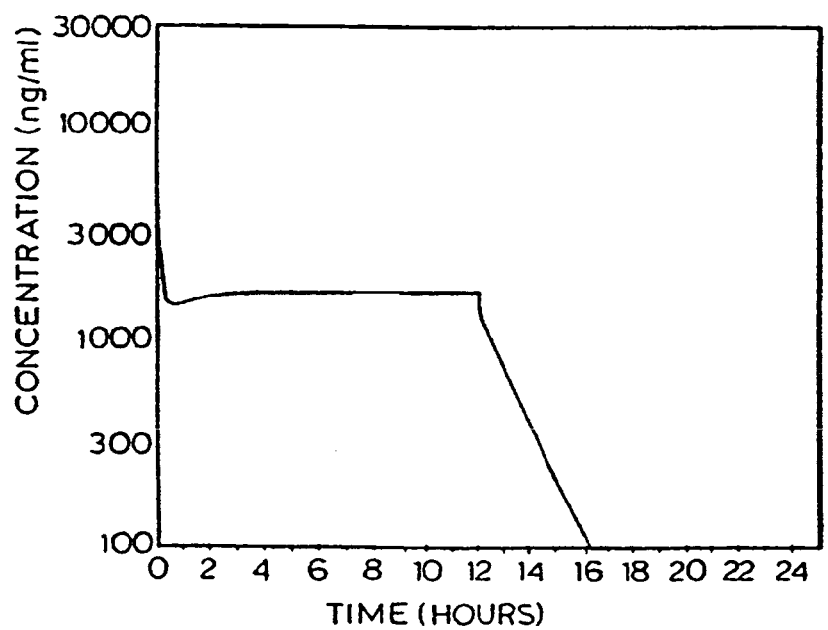

FIGS. 5a and 5b show pharmacokinetic profile of LACI in baboons. Open circles represent results in the immunoassay and closed circles represent results in the bioassay. For example, 0.5 mg/kg of LACI was given as an I.V. bolus over 30 seconds to two healthy baboons. Blood was sampled from animals at +1 minute, 3, 6, 10, 20, 40, 60, 90, 120, 180, 240 and 420 minutes. LACI levels in plasma were measured using both immunoassay and bioassay (described in text). In FIG. 5b, the line represents 0.7 ug/kg+10 ug/kg/min inf. 12 hr.

Figure 6A:
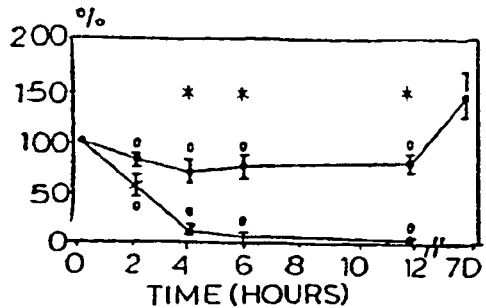
Figure 6E:
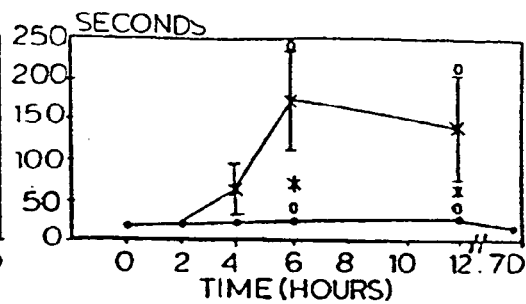
Figure 6B:
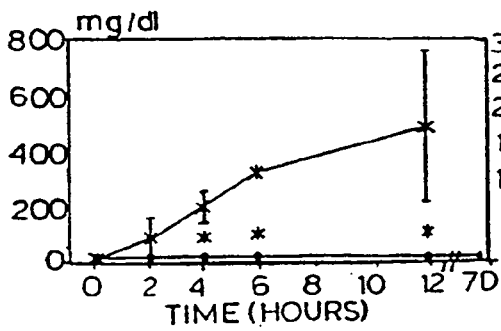
Figure 6F:
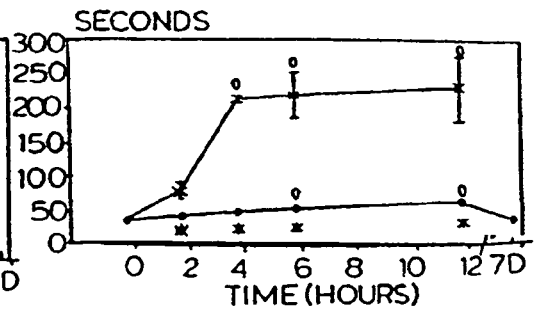
Figure 6C:
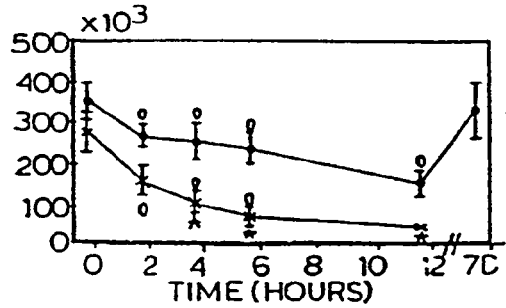
Figure 6G:
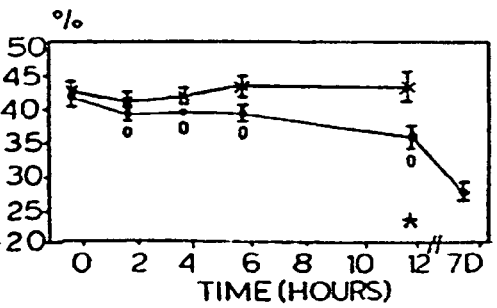
Figure 6D:
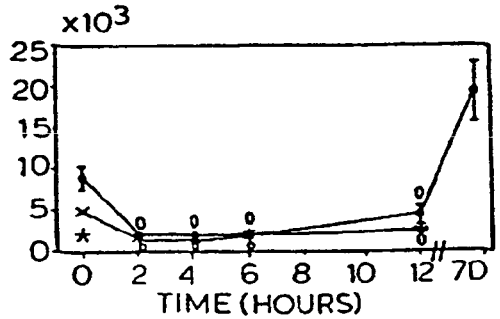
Figure 6H:
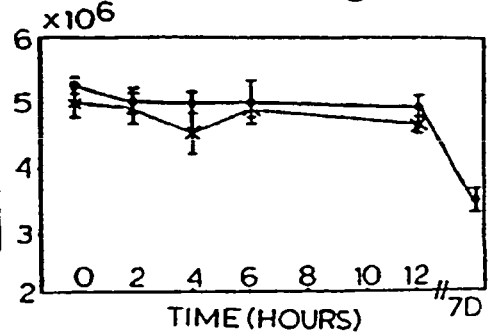

FIGS. 6a through 6h show the coagulation and hematological response to LACI administration 30 minutes after the start of a two hour lethal bacterial intravenous infusion. Lines with solid circles represent results obtained from treated animals and lines with "X"s represent results obtained form control animals. A ★ (star) indicates a statistically significant difference ($p<0.05$) between the control and experimental groups and an open circle represents a statistically significant ($p<0.05$) difference between times. FIG. 6a shows fibrinogen levels, FIG. 6b shows FDP levels, FIG. 6c shows platelet levels, FIG. 6d shows WBC levels, FIG. 6e shows PT levels, Figure ^f shows APTT levels, FIG. 6g shows hemtocrit levels, and FIG. 6h shows RBC levels. For example, anesthetized baboons were challenged with a lethal dose of *E. coli* (~5× $10^{10}$ organisms/kg) intravenously infused over two hours. Thirty minutes after the start of the bacterial infusion five baboons received phosphate buffered saline (PBS; excipient control; *) and the other five received LACI in PBS (●). Blood samples were obtained from the ten baboons before the start of the bacterial infusion, and at 2, 4, 6, and 12 hours after the onset of infusion. Blood samples were assayed for fibrinogen, fibrin degradation products, prothrombin time, activated partial thromboplastin time, and for hematocrit, platelet, red cell and white cell counts by standard methods. Mean ± standard error of each measurement is plotted against time (hrs.).

DETAILED DESCRIPTION OF THE INVENTION

It has now been discovered that LACI in the absence of other anticoagulants such as heparin is effective in the prophylaxis and treatment of sepsis. It has also been discovered that LACI alone is effective in the prophylaxis and treatment of sepsis-associated coagulation disorders such as, for example, DIC. LACI inhibits/attenuates the coagulopathies and the inflammatory process associated with acute inflammatory and septic shock.

LACI is a serum glycoprotein with a molecular weight of 38,000 Kd. It is also known as tissue factor inhibitor because it is a natural inhibitor of thromboplastin (tissue factor) induced coagulation. (U.S. Pat. Nos. 5,110,730 and 5,106,833 describe tissue factor and are hereby incorporated by reference in their entireties). LACI is a protease inhibitor and has 3 Kunitz domains, two of which are known to interact with factors VII and Xa respectively, while the function of the third domain is unknown. Many of the structural features of LACI can be deduced because of its homology with other well-studied proteases. LACI is not an enzyme, so it probably inhibits its protease target in a stoichiometric manner; namely, one of the domains of LACI inhibits one protease molecule. As utilized herein LACI means one or more of the thee Kunitz-type inhibitory domains of lipoprotein-associated coagulation inhibitor which are active in treating sepsis. The domains may be present on fragments of LACI or in hybrid molecules. See U.S. Pat. No. 5,106,833 regarding fragments and muteins. Preferably, Kunitz domains 1 and/or 2 will be present. Kunitz domain 3 is not necessary for activity.

LACI is also known as tissue factor pathway inhibitor (TFPI). This name has been accepted by the International Society on Thrombosis and Hemostasis, Jun. 30, 1991, Amsterdam. TFPI was first purified from a human hepatoma cell, Hep G2, as described by Broze and Miletich; *Proc. Natl. Acad. Sci. USA* 84:1886-1890 (1987), and subsequently from human plasma as reported by Novotny et al., *J. Biol. Chem.* 264:18832-18837 (1989); Chang liver and SK hepatoma cells as disclosed by Wun et al., *J. Biol. Chem.* 265:16096-16101 (1990). TFPI cDNA molecules have been isolated from placental and endothelial cDNA libraries as described by Wun et al., *J. Biol. Chem.* 263:6001-6004 (1988); Girard et al., Thromb. Res. 55, 37-50 (1989). The primary amino acid sequence of TFPI, deduced from the cDNA sequence, shows that TFPI contains a highly negatively charged amino-terminus, three tandem Kunitz-type inhibitory domains, and a highly positively charged carboxyl terminus. The first Kunitz-domain of TFPI (amino acids 19 to 89 of mature TFPI and amino acids 47 to 117 of pre-TFPI) is needed for the inhibition of the factor $VII_a$/tissue factor complex and the second Kunitz-domain of TFPI (amino aicds 90 to 160 of the mature protein or amino acids 118 to 188 of pre-TFPI) is responsible for the inhibition of factor $X_a$ according to Girard et al., *Nature* 328:518-520 (1989), while the function of the third Kunitz-domain (amino acids 182 to 252 of mature TFPI and amino acids 210 to 280 of pre-TFPI) remains unknown. See also U.S. Pat. No. 5,106,833. TFPI is believed to function in vivo to limit the initiation of coagulation by forming an inert, quaternary factor $X_a$: TFPI: factor $VII_a$: tissue factor complex. See reviews by Rapaport, *Blood* 73:359-365 (1989), and Broze et al., *Biochemistry* 29:7539-7546 (1990).

Three truncated versions of LACI have been produced from *E. coli*. These are ala-TFPI-1-160; ala-TFPI-13-161, and ala-TFPI-22-150. These derivatives have production advantages and favorable solubility characteristics compared to full-length ala-TFPI (ala-LACI). The derivatives are produced at levels approximately 7-10 fold higher than full-length ala-LACI. Solubility of the derivatives in a physiological buffer, e.g., phosphate buffered saline, is about 40 to 80-fold higher than full-length ala-LACI. In addition, the clearance rate appears slower for at least one of the derivatives relative to the full-length form. All three forms are active in factor Xa-dependent inhibition of factor VIIa/tissure factor activity. Ala-TFPI-1-160 was tested in a baboon model of sepsis and was found to promote survival. Five of eight animals treated with the fragment survived to the 7 day endpoint, while none of five untreated control baboons survived.

Recombinant TFPI has been expressed as a glycosylated protein using mammalian cell hosts including mouse C127 cells as disclosed by Day et al., *Blood* 76:1538-1545 (1990), baby hamster kidney cells as reported by Pedersen et al., *J. Biol. Chem.* 265:16786-16793 (1990), Chinese hamster ovary cells and human SK hepatoma cells. The C127 TFPI has been used in animal studies and shown to be effective in the inhibition of tissue factor-induced intravascular coagulation in rabbits according to Day et al., supra, and in the prevention of arterial reocclusion after thrombolysis in dogs as described by Haskel et al., *Circulation* 84:821-827 (1991).

Recombinant TFPI also has been expressed as a non-glycosylated protein using *E. coli* host cells yielding a highly active TFPI by in vitro folding of the protein as described below in Example 1.

The cloning of the TFPI cDNA which encodes the 276 amino acid residue protein of TFPI is further described in Wun et al., U.S. Pat. No. 4,966,852, the disclosure of which is incorporated by reference herein.

Figure 1:
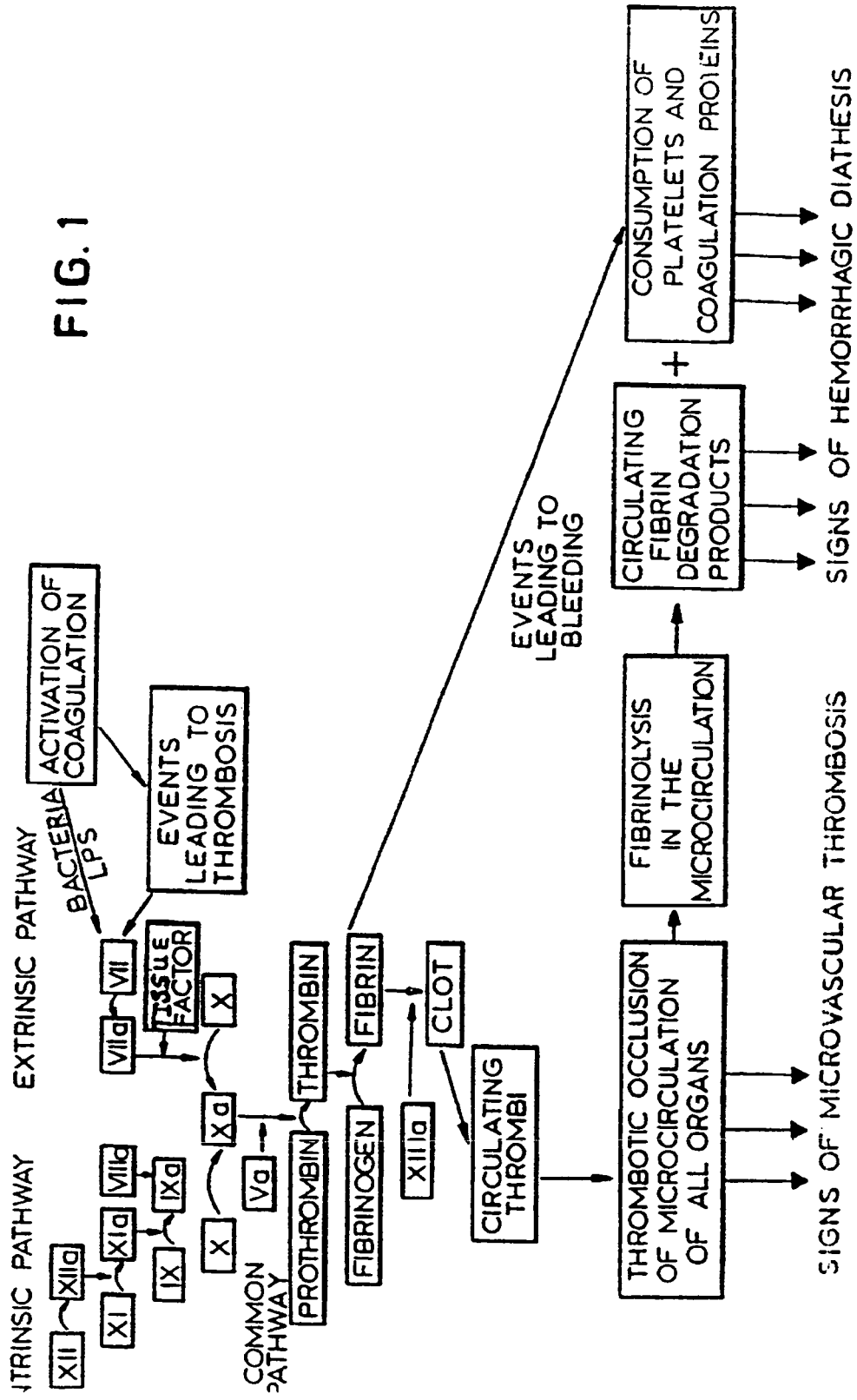

LACI was discovered by Broze et al., 1987, *PNAS (USA)*, 84:1886-1890, and was found to inhibit Factor Xa directly, as well as to inhibit tissue factor activity by formation of an inert factor VIIa/tissue factor (TF)/Factor Xa/Ca++ inhibitor complex. It has the DNA sequence shown in U.S. Pat. No. 4,966,852 which is hereby incorporated by reference in its entirety. A schematic diagram of the proposed mechanism for the inhibition of Factor Xa and VIIa/TF complex by LACI is shown in FIG. 1.

Coagulation occurs via two pathways: intrinsic and extrinsic. The intrinsic and extrinsic pathways of coagulation consist of several proteases that are activated in a series which, unless inhibited, result in the formation of fibrin clots. LACI acts at two steps in the coagulation cascade pathway both at the Xa and VIIa/TF level as described above. The activation of tissue factor, which LACI inhibits, is a relatively early event in extrinsic pathway. (LACI has also been called Extrinsic Pathway Inhibitor (EPI) and tissue factor pathway inhibitor (TFPI)). LACI inactivates Factor Xa which is a common protease for the extrinsic and intrinsic pathway and is downstream from activation of tissue factor.

The concentration of LACI in normal plasma is 100 ng/ml. A report by Bajaj et al., 1987, *J. Clin. Invest.*, 79:1874-1878, suggests that LACI is synthesized in liver and endothelial cells and is consumed during DIC in patients. Specifically, LACI values in the plasma of 15 healthy volunteers ranged from 72 to 142 U/ml with a mean of 101 U/ml. Interestingly, LACI levels of 10 patients with DIC were 57±30 U/ml (p<0.001). In contrast, LACI levels of 12 patients with hepatocellular disease were a mean of 107±33, i.e., similar to normal. Sandset et al., 1989, *J. Internal Med.*, 225:311-316, monitored LACI plasma levels during a 7-day observation period from patients with pneumonia (n=13), and in stroke patients with infarction (n=9), and haemorrhage (n=9). In pneumonia patients, LACI showed a weak but not significant increase in the recovery period (p=0.068). In cerebral haemorrhage patients, LACI levels did not consistently change, while in cerebral infarction patients, an increase in LACI levels was observed from day 1 to day 2 (p<0.05). This latter effect was most probably due to release of tissue bound LACI by heparin and thus, was only observed in heparin-treated patients.

Sandset et al., 1989, *Haemostasis*, 19:189-195, also serially determined LACI levels in 13 patients with post-operative/post-traumatic septicemia. In the survivors (n=8), initial low LACI activity normalized during recovery. In the fatal cases (n=5), a progressive increase in LACI activity (maximal 30±15%) was observed until death. The increase may be explained by a badly damaged endothelium that is releasing the tissue bound LACI into the circulation.

As utilized herein, the term "sepsis" means a toxic condition resulting from the spread of bacterial endotoxins from a focus of infection.

As utilized herein, the term "sepsis-associated coagulation disorder" means a disorder resulting from or associated with coagulation system activation by a bacterial endotoxin, a product of such bacterial endotoxin or both. An example of such sepsis-associated coagulation disorder is disseminated intravascular coagulation.

The term "therapeuticaly-effective amount" as utilized herein means an amount necessary to permit observation of activity in a patient sufficient to alleviate one or more symptoms generally associated with sepsis. Such symptoms include, but are not limited to, death, increased heart rate, increased respiration, decreased fibrinogen levels, decreased blood pressure, decreased white cell count, and decreased platelet count. Preferably, a therapeutically-effective amount is an amount necessary to attenuate a decrease in fibrinogen levels in a patient being treated.

LACI Manufacture

LACI can be made and isolated by several methods. For example, cells that secrete LACI include aged endothelial cells or young endothelial cells which have been treated with TNF for about 3 to 4 days, also hepatocytes or hepatoma cells. LACI can be purified from this cell culture by conventional methods. For example, these methods include the chromatographic methods shown in Pedersen et al., 1990, *J. of Biological Chemistry*, 265:16786-16793, Novotny et al., 1989, *J. of Biological Chemistry*, 264:18832-18837, Novotny et al., 1991, *Blood*, 78:394-400, Wun et al., 1990, *J. of Biological Chemistry*, 265;16096-16101, and Broze et al., 1987, *PNAS (USA)*, 84:1886-1890. Furthermore, LACI appears in the bloodstream and could be purified from blood, see Pedersen et al., supra. However, that method is not suggested or preferred because of the large quantities of blood that would be required to obtain sufficient quantities of LACI.

LACI may be produced recombinantly as shown in U.S. Pat. No. 4,966,852. For example, the cDNA for the protein can be incorporated into a plasmid for expression in prokaryotes or eukaryotes. U.S. Pat. No. 4,847,201, which is hereby incorporated by reference in its entirety, provides details for transforming microorganisms with specific DNA sequences and expressing them. There are many other references known to those of ordinary skill in the art which provide details on expression of proteins using microorganisms. Many of those are cited in U.S. Pat. No. 4,847,201, such as Maniatas, T., et al., 1982, *Molecular Cloning*, Cold Spring Harbor Press.

The following is an overview about transforming and expressing LACI in microorganisms. LACI DNA sequences must be isolated, and connected to the appropriate control sequences. LACI DNA sequences are shown in U.S. Pat. No. 4,966,852 and it can be incorporated into a plasmid, such as pUNC13 or pBR3822, which are commercially available from companies such as Boehringer-Mannheim. Once the LACI DNA is inserted into a vector, it can be cloned into a suitable host. The DNA can be amplified by techniques such as those shown in U.S. Pat. No. 4,683,202 to Mullis and U.S. Pat. No. 4,683,195 to Mullis et al. (LACI cDNA may be obtained by inducing cells, such as hepatoma cells (such as HepG2 and SKHep) to make LACI mRNA then identifying and isolating the mRNA and reverse transcribing it to obtain cDNA for LACI.) After the expression vector is transformed into a host such as *E. coli* the bacteria may be fermented and the protein expressed. Bacteria are preferred prokaryotic microorganisms and *E. coli* is especially preferred. A preferred microorganism useful in the present invention is *E. coli* K-12, strain MM294 deposited with the ATCC on Feb. 14, 1984, under the provisions of the Budapest Treaty. It has accession number 39607. Alternatively, LACI may be introduced into mammalian cells. These mammalian cells may include CHO, COS, C127, Hep G2, SK Hep, baculovirus, and infected insect cells (see also U.S. Pat. No. 4,847,201, referred to above). See also Pedersen et al., 1990, *J. of Biological Chemistry*, 265: 16786-16793.

Some specific details about the production of a recombinant protein typically involves the following:

Suitable Hosts. Control Systems and Methods

First, a DNA encoding the mature protein (used here to include all muteins); the preprotein; or a fusion of the LACI protein to an additional sequence which does not destroy its activity or to additional sequence cleaved under controlled conditions (such as treatment with peptidase) to give an active protein, is obtained. If the sequence is uninterrupted by introns it is suitable for expression in any host. If there are introns, expression is obtainable in mammalian or other eucaryotic systems capable of processing them. This sequence should be in excisable and recoverable form. The excised or recovered coding sequence is then placed in operable linkage with suitable control sequences in a replicable expression vector. The vector is used to transform a suitable host and the transformed host cultured under favorable conditions to effect the production of the recombinant LACI.

Genomic or cDNA fragments are obtained and used directly in appropriate hosts. The constructions for expression vectors operable in a variety of hosts are made using appropriate replications and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, or mammalian cells are presently useful as hosts. Host systems which are capable of proper post-translational processing are preferred. Accordingly, although procaryotic hosts are in general the most efficient and convenient for the production of recombinant proteins, eucaryotic cells, and, in particular, mammalian cells are preferred for their processing capacity, for example, the ability to form the proper glycosylation patterns. In addition, there is more assurance that the native signal sequence will be recognized by the mammalian host cell, thus making secretion possible, and purification thereby easier.

Control Sequences and Corresponding Hosts

Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al., 1977, *Gene*, 2:95. pBR322 contains genes for ampicillin and tetracycline resistance, and thus provides additional markers which can be either retained or destroyed in constructing the desired vector. Commonly used procaryotic control sequences are defined herein to include promoters for transcription initiation, optionally with an operator, along with ribosome binding site sequences, which include such commonly used promoters as the beta-lactamase (penicillinase) and lactose (lac) promoter systems (Chang, et al., 1977, *Nature*, 198:1056) and the tryptophan (trp) promoter system (Goeddel, et al., 1980, *Nucleic Acids Res.*, 8:4057) and the λ derived $P_L$ promoter and N-gene ribosome binding site (Shimatake, et al., 1981, *Nature*, 292: 128), which has been made useful as a portable control cassette, as set forth in U.S. Pat. No. 4,711,845, issued Dec. 8, 1987. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used although a number of other strains are commonly available. Examples of plasmid vectors suitable for yeast expression are shown in Broach, J. R., 1983, *Meth. Enz.*, 101:307; Stinchcomb et al., 1979, *Nature*, 282:39; and Tschempe et al., 1980, *Gene*, 10:157 and Clarke, L., et al., 1983, *Meth. Enz.*, 101:300. Control sequences for yeast vectors include promoters for the synthesis of glycolytic enzymes (Hess, et al., 1968, *J. Adv. Enyme Reg.*, 7:149; Holland, et al., 1978, *Biochemistry*, 17:4900). Additional promoters known in the art include the promoter for 3-phosphoglycerate kinase (Hitzeman, et al., 1980, *J. Biol. Chem.*, 255:2073), and those for other glycolytic enzymes, such as glyceraldehyde-3-phosphate dehydrogenase, hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra). It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J. et al., 1981, *J. Biol. Chem.*, 256:1385) or the LEU2 gene obtained from YEp13 (Broach, J. et al., 1978, *Gene*, 8:121), however, any vector containing a yeast compatible promoter, origin of. replication and other control sequences is suitable.

It is also, of course, possible to express genes encoding polypeptides in eucaryotic host cell cultures derived from multicellular organisms. See, for example, *Tissue Culture*, 1973, Cruz and Patterson, eds., Academic Press. Useful host cell lines include murine myelomas N51, VERO, HeLa cells, Chinese hamster ovary (CHO) cells, COS, C127, Hep G2, SK Hep, baculovirus, and infected insect cells. Expression vectors for such cells ordinarily include promoters and control sequences compatible with mammalian cells such as, for example, the commonly used early and later promoters from Simian Virus 40 (SV40) (Fiers, et al., 1978, *Nature*, 273:113), or other viral promoters such as those derived from polyoma, Adenovirus 2, bovine papilloma virus, or avian sarcoma viruses, or immunoglobulin promoters and heat shock promoters. General aspects of mammalian cell host system transformations have been described by Axel, U.S. Pat. No. 4,399, 216, issued Aug. 16, 1983. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al., 1982, *J. Mol. Appl. Gen.*, 1:561) are available. Methods and vectors for transformation of plant cells have been disclosed in PCT Publication No. WO 85/04899, published Nov. 7, 1985.

Host strains useful for cloning and sequencing, and for expression of construction under control of most bacterial promoters include *E. coli* strain MM294 obtained from *E. coil* Genetic Stock Center GCSC #6135. For expression under control of the $P_LN_{RBS}$ promoter, *E. coli* strain K12 MC1000 lambda lysogen, $N_7N_{53}cI857$ SusP80, a strain deposited with the American Type Culture Collection (ATCC 39531), may be used. *E. coli* DG116, which was deposited with the ATCC (Accession No. 53606) on Apr. 7, 1987, may also be used. For M13 phage recombinants, *E. coli* strains susceptible to phage infection, such as *E. coli* K12 strain DG98, can be employed. The DG98 strain has been deposited with the ATCC (ATCC 39768) on Jul. 13, 1984. Mammalian expression can be accomplished in COS-A2 cells, COS-7, CV-1, murine myelomas N51, VERO, HeLa cells, Chinese hamster ovary (CHO) cells, COS, C127, Hep G2, SK Hep, baculovirus, and infected insect cells. Insect cell-based expression can be in *Spodoptera frugiperda*.

Transformations

Depending on the host cell used, transformation is done using standard techniques appropriate to such cells. The calcium treatment employing calcium chloride, as described by Cohen, S. N., 1972, *PNAS (USA)*, 69:2110, is used for procaryotes or other cells which contain substantial cell wall barriers. Infection with *Agrobacterium tumefaciens* (Shaw, C. H. et al., 1983, *Gene*, 23:315) is used for certain plant cells. For mammalian cells without such cell walls, the calcium phosphate precipitation method of Graham and van der Eb, 1987, *Virology*, 52:546 is preferred. Transformations into yeast are carried out according to the method of Van Solingen, P. et al., 1977, *J. Bact.*, 130:946 and Hsiao, C. L. et al., 1979, *PNAS (USA)*, 76:3829.

Probing mRNA by Northern Blot: Probe of cDNA or Genoinic Libraries

RNA is fractionated for Northern blot by agarose slab gel electrophoresis under fully denaturing conditions using formaldehyde, Maniatas, T., et al., 1982, *Molecular Cloning*, Cold Spring Harbor Press, pp. 202-203, or 10 mM methyl mercury ($CH_3HgOH$) (Bailey, J. M., et al., 1976, *Anal. Biochem.*, 70: 75-85; Shegal, P. B. et al., 1980, *Nature*, 288:95-97) as the denaturant. For methyl mercury gels, 1.5% gels are prepared by melting agarose in running buffer (100 mM boric acid, 6 mM sodium borate, 10 mM sodium sulfate, 1 mM EDTA, pH 8.2), cooling to 60° C. and adding 1/100 volume of 1 M $CH_3HgOH$. The RNA is dissolved in 0.5× running buffer and denatured by incubation in 10 mM methyl mercury for 10 minutes at room temperature. Glycerol (20%) and bromophenol blue (0.05%) are added for loading the samples. Samples are electrophoresed for 500-600 volt-hr with recirculation of the buffer. After electrophoresis, the gel is washed for 40 minutes in 10 mM 2-mercaptoethanol to detoxify the methyl mercury, and Northern blots prepared by transferring the RNA from the gel to a membrane filter.

cDNA or genomic libraries are screened using the colony or plaque hybridization procedure. Bacterial colonies, or the plaques for phage, are lifted onto duplicate nitrocellulose filter papers (S&S type BA-85). The plaques or colonies are lysed and DNA is fixed to the filter by sequential treatment for 5 minutes with 500 mM NaOH, 1.5 M NaCl. The filters are washed twice for 5 minutes each time with 5× standard saline citrate (SSC) and are air dried and baked at 80° C. for 2 hours.

The gels for Northern blot or the duplicate filters for cDNA or genomic screening are prehybridized at 25° to 42° C. for 6 to 8 hours with 10 ml per filter of DNA hybridization buffer without probe (0-50% formamide, 5-6×SSC, pH 7.0, 5× Denhardt's solution (polyvinylpyrrolidone, plus Ficoll and bovine serum albumin; 1×=0.02% of each), 20-50 mM sodium phosphate buffer at pH 7.0, 0.2% sodium dodecyl sulfate (SDS), 20 μg/ml poly U (when probing cDNA), and 50 μg/ml denatured salmon sperm DNA). The samples are then hybridized by incubation at the appropriate temperature for about 24-36 hours using the hybridization buffer containing kinased probe (for oligomers). Longer cDNA or genomic fragment probes were labelled by nick translation or by primer extension.

The conditions of both prehybridization and hybridization depend on the stringency desired, and vary, for example, with probe length. Typical conditions for relatively long (e.g., more than 30-50 nucleotide) probes employ a temperature of 42° to 55° C. and hybridization buffer containing about 20%-50% formamide. For the lower stringencies needed for oligomeric probes of about 15 nucleotides, lower temperatures of about 25°-42° C., and lower formamide concentrations (0%-20%) are employed. For longer probes, the filters may be washed, for example, four times for 30 minutes, each time at 40°-55° C. with 2×SSC, 0.2% SDS and 50 mM sodium phosphate buffer at pH 7, then washed twice with 0.2×SSC and 0.2% SDS, air dried, and are autoradiographed at −70° C. for 2 to 3 days. Washing conditions are somewhat less harsh for shorter probes.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by 1 unit of enzyme in about 20 μl of buffer solution; in the examples herein, typically, an excess of restriction enzyme is used to insure complete digestion of the DNA substrate. Incubation times of about 1 hour to 2 hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods of Enzymology*, 65:499-560, 1980.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° to 25° C. in 50 mM dithiothreitol (DTT) and 5-10 μM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared by the triester method of Matteuccei et al., 1981, *J. Am. Chem. Soc.*, 103:

3185-3191, or using automated synthesis methods. Kinasing of single strands prior to annealing or for labelling is achieved using an excess, e.g., approximately 10 units of polynucleotide kinase to 1 nmole substrate in the presence of 50 mM Tris, pH 7.6, 10 mM MgCl$_2$, 5 mM DTT, 1-2 mM ATP. If kinasing is for labelling of probe, the ATP will contain high specific activity 32YP.

Ligations are performed in 15-30 μl volumes under the following standard conditions and temperatures: 20 mM Tris-Cl pH 7.5, 10 mM MgCl$_2$, 10 mM DTT, 33 μg/ml bovine serum albumin (BSA), 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In the vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^{2+}$ and Mg$^{2+}$ using about 1 unit of BAP per μg of vector at 60° C. for about 1 hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Modification of DNA Sequences

For portions of vectors derived from cDNA or genomic DNA which require sequence modifications, site specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form: 50% will have the original sequence. The plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Verification of Construction

Correct ligations for plasmid construction could be confirmed by first transforming E. coli strain MM294, or other suitable host, with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B. et al., 1969, PNAS (USA), 62:1159, optionally following chloramphenicol amplification (Clewell, D. B., 1972, J. Bacteriol, 110:667). The isolated DNA is analyzed by restriction and/or sequenced by the dideoxy method of Sanger, F., et al., 1977, PNAS (USA), 74:5463 as further described by Messing et al., 1981, Nucleic Acids Res., 9:309, or by the method of Maxam et al., 1980, Methods in Enzymology, 65:499.

Purification of LACI

For purification of mammalian cell expressed LACI, the following methods may be used: sequential application of heparin-Sepharose, MonoQ, MonoS, and reverse phase HPLC chromatography. See Pedersen et al., supra, Novotny et al., 1989, J. of Biological Chemistry, 264:18832-18837, Novotny et al., 1991, Blood, 78:394-400, Wun et al., 1990, J. of Biological Chemistry, 265:16096-16101, and Broze et al., 1987, PNAS (USA), 84:1886-1890. These references describe various methods for purifying mammalian produced LACI.

Additionally, LACI may be produced in bacteria, such as E. coli, and subsequently purified. Generally, the procedures shown in U.S. Pat. Nos. 4,511,502; 4,620,948; 4,929,700; 4,530,787; 4,569,790; 4,572,798; and 4,748,234 can be employed. These patents are hereby incorporated by reference in their entireties. Typically, the heterologous protein (i.e. LACI) is produced in a refractile body within the bacteria. To recover and purify the protein, the cells are lysed and the refractile bodies are centrifuged to separate them from the cellular debris (see U.S. Pat. No. 4,748,234 for lowering the ionic strength of the medium to simplify the purification). Thereafter, the refractile bodies containing the LACI are denatured, at least once (typically in reducing environment), and the protein is oxidized and refolded in an appropriate buffer solution for an appropriate length of time. LACI has a significant number of cysteine residues and the procedure shown in U.S. Pat. No. 4,929,700 should be relevant because CSF-1 also contains a significant number of cysteine residues. LACI may be purified from the buffer solution by various chromatographic methods, such as those mentioned above for the mammalian cell derived LACI. Additionally, the methods shown in U.S. Pat. No. 4,929,700 may be employed.

Administration and Formulations

LACI is administered at a concentration that is therapeutically effective to treat and prevent sepsis, acute or chronic inflammation, and other diseases in which cytokines up-regulate tissue factor. To accomplish this goal, LACI is preferably administered intravenously. Methods to accomplish this administration are known to those of ordinary skill in the art.

Before administration to patients, formulants may be added to LACI. A liquid formulation is preferred. In the example below, LACI was formulated in 150 mM NaCl and 20 mM NaPO$_4$ at pH 7.2. However, LACI may be formulated at different concentrations or using different formulants. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcelloluose, or mixtures thereof. Sucrose is most preferred. Sugar alcohol is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Preferably, the concentration is from 0.01 to 0.3 molar. Surfactants that can be added to the formulation are shown in EP Nos. 270,799 and 268,110.

Additionally, LACI can be chemically modified by covalent conjugation to a polymer to increase its circulating half-life, for example. Preferred polymers, and methods to attach them to peptides, are shown in U.S. Pat. Nos. 4,766,106, 4,179,337, 4,495,285, and 4,609,546 which are all hereby incorporated by reference in their entirties. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/IL-2 of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064-15070, and a discussion of POG/IL-2 conjugates is found in U.S. Pat. No. 4,766,106, both of which are hereby incorporated by reference in their entireties.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in water. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. A preferred injectable preparation solution is LACI in an aqueous solution of 150 mM sodium chloride and 20 mM sodium phosphate.

While LACI can be administered as the sole active anticoagulation pharmaceutical agent, it can also be used in combination with one or more antibodies useful for treating sepsis, such as, for example, anti-endotoxin, monoclonal antibodies (endotoxin-binding Mabs) and anti-TNF products such as an anti-TNF murine Mab. LACI can also be combined with interleukin-1 receptor antagonists, bactericidal/permeability increasing (BPI) protein, immunostimulant, compounds having anti-inflammatory activity, such as PAF antagonists and cell adhesion blockers. When administered as a combination, the therapeutic agents can be formulated as separate compositions which are given at the same time or different times, or the therapeutic agents can be given as a single composition.

LACI may he given in combination with other agents which would be effective to treat sepsis. For example, the following may be administered in combination with LACI: antibiotics that can treat the underlying bacterial infection; monoclonal antibodies that are directed against bacterial cell wall components; receptors that can complex with cytokines that are involved in the sepsis pathway; and generally any agent or protein that can interact with cytokines or complement proteins in the sepsis pathway to reduce their effects and to attenuate sepsis or septic shock.

Antibiotics that are useful in the present invention include those in the general category of: beta-lactam rings (penicillin), amino sugars in glycosidic linkage (aminoglycosides), macrocyclic lactone rings (macrolides), polycyclic derivatives of napthacenecarboxamide (tetracyclines), nitrobenzene derivatives of dichloroacetic acid, peptides (bacitracin, gramicidin, and polymyxin), large rings with a conjugated double bond system (polyenes), sulfa drugs derived from sulfanilamide (sulfonamides), 5-nitro-2-furanyl groups (nitrofurans), quinolone carboxylic acids (nalidixic acid), and many others. Other antibiotics and more versions of the above specific antibiotics may be found in Encyclopedia of Chemical Technology, 3rd Edition, Kirk-Othymer (ed.), Vol. 2, pages 782-1036 (1978) and Vol. 3, pages 1-78, Zinsser, *MicroBiology*, 17th Edition W. Joklik et al. (Eds.) pages 235-277 (1980), or Dorland's Illustrated Medical Dictionary, 27th Edition, W. B. Saunders Company (1988).

Monoclonal antibodies that may be administered along with LACI include those found in PCT WO 88/03211, to Larrick et al., entitled Gram-Negative Bacterial Endotoxin Blocking Monoclonal Antibodies, and U.S. Ser. No. 07/876,854, filed Apr. 30, 1992, to Larrick et al. Both applications disclose specific monoclonal antibodies that are useful to treat sepsis and which bind to various antigens on the *E. coli* bacterial cell wall. A specifically preferred monoclonal antibody is that which is produced by hybridoma ATCC No. HB9431.

Other agents which may be combined with LACI include monoclonal antibodies directed to cytolines involved in the sepsis pathway, such as those monoclonal antibodies directed to IL-6 or M-CSF, see U.S. Ser. No. 07/451,218, filed Dec. 15, 1989 to Creasey et al. and monoclonal antibodies directed to TNF, see Cerami et al., U.S. Pat. No. 4,603,106; inhibitors of protein that cleave the mature TNF prohormone from the cell in which it was produced, see U.S. Ser. No. 07/395,253, filed Aug. 16, 1989, to Kriegler et al.; antagonists of IL-1, such as shown in U.S. Ser. No. 07/517,276, filed May 1, 1990 to Haskill et al.; inhibitors of IL-6 cytokine expression such as inhibin, as shown in U.S. Ser. No. 07/494,624, filed Mar. 16, 1992, to Warren et al.; and receptor based inhibitors of various cytokine such as IL-1. Antibodies to complement or protein inhibitors of complement, such as $CR_1$, DAF, and MCP After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, LACI is useful to therapeutically or prophylactically treat human patients with sepsis or septic shock, with or without DIC. Generally, people having sepsis are characterized by high fever (>38.5° C.) or hypothermia (<35.5° C.), low blood pressure, tachypnea (>than 20 breaths/minute), tachycardia (>than 100 beats/minute), leukocytosis (>15,000 cells/mm$^3$) and thrombocytopenia (<than 100,000 platelets/mm$^3$) in association with bacteremia. LACI should be administered as soon as a patient is suspected of being septic; presenting themselves with a greater than or equal to 20% drop in fibrinogen or appearance of fibrin split products, a rise in the patient's temperature and the diagnosis of leukopenia, thrombocytopenia and hypotension associated with sepsis. LACI should also be administered when there is a risk of sepsis, for example, from a gunshot wound, or from a surgical incision. As also stated above, the preferred route is by intravenous administration. Generally, LACI is given at a dose between 1 μg/kg and 20 mg/kg, more preferably between 20 μg/kg and 10 mg/kg, most preferably between 1 and 7 mg/kg.

Total daily dose administered to a host in single or divided doses may be in amounts, for example, from about 2 to about 50 mg/kg body weight daily and more usually 4 to 20 mg/kg, preferably, from about 6 to about 10 mg/kg. Dosage unit compositions may contain such amounts or submultiples thereof to make up the daily dose. Lower amounts may be useful for prophylactic or other purposes, for example, from 1 μg/kg to 2 mg/kg. The amount of active ingredient that may be combined with the carrier materials to produce a single dosage form will vary depending upon the patient treated and the particular mode of administration.

The dosage regimen is selected in accordance with a variety of factors, including the type, age, weight, sex, diet and medical condition of the patient, the severity of the condition, the route of administration, pharmacological considerations such as the activity, efficacy, pharmacokinetic and toxicology profiles, whether a drug delivery system is utilized and whether the compound is administered as part of a drug combination. Thus, the dosage regimen actually employed may vary widely and therefore may deviate from the preferred dosage regimen set forth above.

Preferably, LACI is given as a bolus dose, to increase circulating levels by 10-20 fold for 4-6 hours after the bolus dose. Continuous infusion may also be used after the bolus dose. If so, LACI may be infused at a dose between 5 and 20 μg/kg/minute, more preferably between 7 and 15 μg/kg/minute.

Generally, LACI may be useful for those diseases that occur due to the up-regulation of tissue factor brought on by TNF, IL-1 or other cytokines. For example, in the examples below, LACI administration is shown to lower the IL-6 concentration. Since IL-6 is one factor that is involved in acute or chronic inflammation, LACI administration is useful for treating inflammation. Typical inflammatory conditions that can be treated by LACI include: arthritis, septic shock, reperfusion injury, inflammatory bowel disease, acute respiratory disease, trauma, and burn.

In treating chronic or acute inflammation, LACI may be administered in the same fashion and at the same doses as in the anti-sepsis method.

The present invention will now be illustrated by reference to the following examples which set forth particularly advantageous embodiments. However, it should be noted that these embodiments are illustrative and are not to be construed as restricting the invention in any way.

EXAMPLES

Example 1

This example illustrates a method for obtaining LACI (TFPI).

Materials

Urea (sequenal grade) and Brij 35 non-ionic surfactant were obtained from Pierce. Mixed bed resin AG501-X8 cation exchanger was purchased from Bio Rad. Mono Q HR 5/5 and HiLoad Q Sepharose anion exchange resins, and Mono S HR 5/5 and Mono S HR 10/16 cation exchange resins were obtained from Pharmacia Thromboplastin reagent (Simplastin Excel) was from Organon Teknika Corp. Bovine factor $X_a$ and Spectrozyme $X_a$ were supplied by American Diagnostica, Inc. SDS-PAGE 10-20% gradient gel was obtained from integrated Separation Systems.

Methods

Expression Vectors and Cloning Strategies

A full length human TFPI cDNA [Wun et al., J. Biol. Chem. 263, 6001-6004 (1988)] was cloned into M13mp18 phage DNA cloning vector as a 1.4 Kb EcoRI fragment. Site-directed mutagenesis [Kunkel et al., *Proc. Nat. Acad. Sci. USA* 32, 488-492 (1985)] was used to introduce an NcoI site at the initiating ATG. The TFPI gene was then cloned as an NcoI/blunted MaeIII fragment into pMON5557 with NcoI and blunted HindIII ends resulting in the new vector pMON9308. MaeIII site is 15 bp downstream from the stop codon in the TFPI cDNA. The expression vector contained the recA promoter, a translational enhancer element and ribosome binding site derived from the gene 10 leader of bacteriophage T7 as described by Olins and Rangwala, *J. Biol. Chem.* 264, 16973-16976 (1989), and the T7 transcription terminator. This plasmid also contains an irrelevant sequence, i.e. the bST gene (bovine somatotropin).

The NcoI/NsiI fragment of pMON9308 was then replaced by a synthetic DNA fragment designed to (1) introduce an alanine encoding codon at the second position, (2) increase the A-T richness of the 5' portion of the gene, and (3) improve E. coli codon usage. Four oligonucleotides, two for each strand, were used. All base substitutions (indicated in upper case), are silent changes. ECTFPI 2 and 3 were 5' phosphorylated [Maniatis et al., *Molecular Cloning: A Laboratory Manual*, Cold Spring Harbor Laboratory, Cold Spring Harbor, N.Y. (1982)]. ECTFPI 1 and 2 and ECTFPI 3 and 4 were annealed in the kinase buffer by incubating for 5 minutes at 70° C. and slow-cooling to room temperature. These fragments were cloned into pMON9308 which had been digested with NcoI/NsiI. PCR amplification was used to introduce a HindIII site as well as a TAA termination codon at the 3' end of the TFPI gene. The PCR primers TPFIterm and TPFIterm 2 are shown below. The TFPI gene was then moved as a NCOI/HindIII fragment into pMON5766. The resultant plasmid was pMON6870.

```
            N
            c
            o         ECTFPI 1
            1
    catggctgattctgaAgaagatgaagaacaTacTa
            cgactaagactTcttctacttcttgtAtgAtaatagtgA

ECTFPI 2

N
                                s
                      ECTFPI 3  i
                                1
    ttatcacTgatacTgaACtgccaccGctgaaactGatgca
            ctatgActTGacggtggCgactttgaCt

ECTFPI 4

HindIII
    TFPIterm:    ataaca[aagctt]acatatttt

NcoI
    TFPIterm2:   atatat[ccatgg]ctgattct
``` pMON6870 was digested with BglII/HindIII. This fragment, containing the expression cassette, was cloned into pMON6710 [Obukowicz et al., Biochemistry 29, 9737-9745 (1990)] which had been digested with BglII/HindIII. The resultant plasmid, pMON6875, includes the tac promoter, G10 leader from bacteriophage T7, met-ala TFPI, and the p22 transcriptional terminator. The plasmids were transformed into MON105 (rpoD+rpoH358) containing F' from JM101 for the expression of TFPI protein.

Fermentation

Ten liter fermentations were run in M9 minimal salts media supplemented with 20 g/l casamino acids in Biostad E fermentors (B. Braun). Fermentations were run at a temperature of 37° C., 1000 rpm agitation, an air flow rate of 15 l/min and 10 psi backpressure. pH was controlled at 7.0 with ammonium hydroxide. Residual glucose concentration in the fermentation broth was automatically controlled at 1.0+/−0.1 g/l. At an optical density of 46.0 at 550 nm, the temperature was shifted from 37° C. to 30° C. and isopropyl β-D thiogalactopyranoside (IPTG) was added to the fermentor to a final concentration of 1.0 mM. The culture was harvested four hours post-induction by concentration in an Amicon DC10L concentrator followed by centrifugation in a Beckman J2-21 centrifuge. The 10-liter fermentation yield 335-456 g (average of 376+/−46 g, n=6) wet weight of cell paste. The cell paste was frozen at −80° C. for further processing hereinbelow.

Isolation of Inclusion Bodies

Frozen E. coli cell paste was resuspended in cold Milli-Q water at a concentration of 75 g/l. The cells were thoroughly dispersed with a homogenizer (Ultra-Turrax model SD-45) for 30 minutes on ice. The cells were mechanically lysed by three passes through the Manton-Gaulin homogenizer (model 15M-8TA) at 12,000 psi. Inclusion bodies were centrifuged in the Sorvall RC-2B centrifuge in the GSA rotor at 10,000 rpm (16,270×g) for 20 minutes. The supernatant was discarded. The inclusion body pellets were collected, resuspended in 1 liter of cold Milli-Q water and dispersed with the Ultra-Turrax homogenizer for 30 minutes on ice. The inclusion bodies were cycled through the Manton-Gaulin homogenizer two more times on ice. Inclusion bodies were pelleted in the Sorvall RC-2B centrifuge as before. Approximately 60 mg of inclusion bodies were collected for every gram of E. coli cells lysed. The inclusion bodies were stored at −80° C.

Buffer Preparation

All the buffers used for sulfonation and refolding of E. coli TFPI contained high concentrations of urea. Urea solutions were treated with Bio-Rad mixed bed resin AG501-X8 at room temperature for at least 20 minutes and filtered through 0.2 μm filter before mixing with buffers. All the solutions used for chromatography were 0.2 μm filtered and sonicated under house vacuum for about 10 minutes.

Sulfonation of Inclusion Bodies

One gm of inclusion bodies (wet weight) was dispersed in 40 ml of a solution containing 50 mM Tris/HCl, pH 8, and 7.5 M urea by homogenization and vortexing. After the inclusion bodies were largely dissolved, 800 mg of sodium sulfite was added and the mixture was shaken at room temperature for 30 minutes. Then, 400 mg of sodium dithionite or 120 mg of sodium tetrathionate was added and the mixture was shaken at 4° C. overnight. The solution dialyzed against 800 ml of a solution containing 20 mM Tris/HCl, pH 8, and 6 M urea for more than 5 hours at 4° C. using a Spectrapor #2 membrane. The dialyzed solution was centrifuged at 48,400×g for 1 hour, filtered through a 0.2 μm filter, divided into aliquots, and stored at −80° C.

Anion-Exchange Chromatography of Sulfonated TFPI

On a small scale, the sulfonated and dialyzed inclusion bodies were fractionated on a Mono Q HR5/5 anion exchange column. The column was pre-equilibrated in Q-buffer (20 mM Tris/HCl, pH 8, 6 M urea, 0.01% Brij 35 non-ionic surfactant) containing 0.15 M NaCl. Two ml of sulfonated inclusion bodies were loaded onto the column. The column was washed with 15 ml of the equilibration buffer and eluted with a 30-ml gradient (0. 15-0.4 M NaCl) in Q-buffer. Fractions of 1 ml were collected. On a larger scale, 40 ml of sulfonated sample (equivalent to 0.56 g of wet weight inclusion body) was loaded onto a HiLoad Q Sepharose 16/10 anion exchange column pre-equilibrated in Q-buffer containing 0.15 M NaCl. The column was washed with 240 ml of equilibration buffer and then eluted with a 396-ml gradient (0.15-0.4 M NaCl) in Q-buffer. Nine ml fractions were collected. Both chromatographies were carried out on a Pharmacia FPLC system at room temperature.

Refold of Sulfonated TFPI

The sulfonated, full-length TFPI pool from anion-exchange chromatography was diluted to an absorbance of 0.07 O.D. units at 280 nm with Q-buffer containing 0.3 M NaCl. Solid L-cysteine was added to a final concentration of 2 mM. The solution was incubated at room temperature for 24 hours, diluted 1:1 with water, 1 mM L-cysteine was added, incubated at room temperature for another 24 hours and then incubated at 4° C. for up to 4 to 8 days. pH was maintained at 8.5 by addition of 50 mM Tris.

Mono S Chromatography of Refold Mixture

In analytical runs, 2 ml refold mixture was loaded onto a Mono S HR 5/5 cation exchange column pre-equilibrated in S-buffer (20 mM sodium phosphate, pH 6.4, 6 M urea). The column was washed with 10 ml of the equilibration buffer and eluted with a 70-ml gradient consisting of 0-0.7 M NaCl in S-buffer. One-ml fractions were collected. In preparative runs, the refold mixture was acidified to pH 4.5, concentrated 75-fold, and loaded onto a Mono S HR10/16 anion exchange column pre-equilibrated in S-buffer containing 0.3 M NaCl. The column was washed with 15-column volumes of the equilibration buffer and eluted with a 0.3-0.5 M NaCl gradient in S-buffer.

Tissue Factor-Induced Coagulation Time Assay

Conventional coagulation time assay was performed using a Fibrometer (Becton Dickinson) clot timer. Ninety μl of human pooled plasma was mixed with 10 μl of TFPI sample or control buffer in the well at 37° C. for 1 min and 0.2 ml of tissue factor (Simplastin Excel, diluted 1:60 into a solution containing 75 mM NaCl, 12.5 mM $CaCl_2$, and 0.5 mg/ml bovine serum albumin) was added to initiate the clotting reaction.

Amidolytic Assay of Factor $X_a$ Inhibitory Activity

Inhibitory activity against bovine factor $X_a$ of TFPI samples were assayed by conventional amidolysis of Spectrozme $X_a$ as described previously by Wun et al., *J. Biol. Chem.* 265, 16096-16101 (1990) except that the assay buffer consisted of 0.1 M Tris/HCl, pH 8.4, and 0.1% Triton X-100 non-ionic surfactant.

Protein Determination

The concentration of protein was determined by absorbance at 280 nm and by quantitative amino acid analysis after HCl/vapor phase hydrolysis at 110° C. for 24 hours.

Sodium Dodecyl Sulfate-Polyacrylamide Gel Electrophoresis (SDS-PAGE)

Daiichi precasted 10-20% gradient gels were used for SDS-PAGE. Samples are either unreduced and not boiled or reduced in 3.3% 2-mercaptoethanol and boiled for 3 minutes before electrophoresis. The gels were stained by Coomassie blue.

Expression of TFPI in *E. coli*

Three vectors were constructed and used for expression of TFPI in *E. coli*. The first construct, pMON9308, which contained the original human TFPI cDNA sequence (except the initiating ATG) and the rec A promoter, achieved a very low level of expression (<0.5% of total cell protein). The second construct, pMON6870, which was similar. to the first but was altered by introducing an alanine at the second position, by increasing the A-T richness of the 5'-end and by improving *E. coli* codon usage, did not significantly raise the expression level. The third construct pMON6875, which was similar to the second but used a tac promoter, achieved an expression level of approximately 5-10% of total cell protein and was used for further tests herein. The majority of TFPI (>90%) appeared to be sequestered in inclusion bodies.

Sulfonation of Inclusion Body and Purification of Full-Length Sulfonated TFPI

In initial tests, it was found that the *E. coli* lysate or the isolated inclusion bodies contained very little TFPI activity as measured by anti-factor $X_a$ and by tissue factor-induced coagulation time assays. Refolding of TFPI by reduction/reoxidation and by sulfonation/disulfide interchange of the crude, solubilized inclusion bodies resulted in very low recovery of activity. Therefore, attempts were made to purify TFPI prior to refolding step, by sulfonation followed by anion exchange chromatography, taking advantage of the 18 added negatively charged groups on the sulfonated TFPI. The sulfonated inclusion bodies were first fractionated on an analytical Mono Q HR5/5 anion exchange column. The flow-through and early gradient fractions contained much of the contaminants *E. coli* protein and truncated TFPI protein (the latter are lower in molecular weight and are immuno-reactive against anti-TFPI-Ig). The full-length TFPI-S-sulfonate eluted at about 0.28 M NaCl. The fractionation of sulfonated inclusion bodies was scaled up 20 times using a Hiload Q Sepharose 16/10 anion exchanger. The chromatogram appeared somewhat different from that from Mono Q but the fractionation of the full-length TFPI-S-sulfonate appeared comparable as judged from SDS-PAGE.

Refold of TFPI-S-sulfonate

Sulfonated TFPI underwent spontaneous refolding and oxidation upon mixing with a suitable concentration of L-cysteine. The efficiency of refold as reflected in the increase of TFPI activity varies widely depending on the refold conditions. Numerous refold conditions were compared and optimized in terms of temperature, pH, urea, L-cysteine and protein concentration. A 2-stage refold process appeared to be the best. In the first stage, the full-length TFPI-S-sulfonate pool was adjusted to an absorbance at 280 nm of 0.07 O.D. units, 2 mM of fresh L-cysteine was added, and the mixture was incubated at room temperature for 24 hours. During this period, the TFPI activity increased from 0 to about 12% of full-length SK hepatoma TFPI which served as a standard for comparison. In the second stage, the solution was diluted 1:1 with water, and fresh L-cysteine was added to a final concentration of 1 mM. The mixture was incubated at room temperature for 24 hours, during which time the specific activity increased about 2 fold to about 30% that of SK Hepatoma TFPI. The solution was then left at 4° C. for several days during which time the TFPI activity increased.

Fractionation of Refold Mixture by Mono S Chromatography

The specific activity of the refold mixture was lower than the purified mammalian SK TFPI which suggests that the former may contain both correctly folded and misfolded molecules or only partially active misfolded molecules. The refold mixture was fractionated on an analytical Mono S cation exchange column. When the UV-absorbing fractions were analyzed for TFPI activity, the highest specific activity was associated with a sharp peak (fraction 52) eluted at 0.52 M NaCl. All the other fractions had a specific activity less than 30% that of fraction 52. SDS-PAGE analysis showed that fraction 52 contained a sharp band and all other fractions, together with pre-column refold mixture, consisted of diffuse, multiple bands under nonreducing condition. The diffuse bands are apparently mainly full-length TFPI in various folded forms since they become sharp-banded upon reduction (see the last two lanes on the right). By making the gradient more shallow, the resolution of the peaks become better and all the protein peaks appeared to elute at lower NaCl concentrations Further, it was possible to wash out the majority of the low-activity peaks with 10 column volumes of 0.3 M NaCl before eluting the active peak with a shadow gradient.

Based on the above results, the chromatography was scaled up using a Mono S HR10/16 cation exchange column. The column was washed with 15 column volumes of 0.3 M NaCl which essentially washed out all low activity peaks. Afterwards, a shadow gradient eluted a peak of protein that contained the active TFPI. SDS-PAGE analysis shows that the peak gave a sharp band under either reducing or non-reducing conditions. The reduced and boiled protein migrated somewhat slower in SDS-PAGE.

Stoichiometry of the Interaction of Refolded TFPI with Factor $X_a$

Inhibition of bovine factor $X_a$ by the active refolded *E. coli* TFPI was examined by measuring the residual amidolytic activity using Spectrozyme $X_a$. The molar ratio of TFPI to bovine factor $X_a$ that resulted in the complete inhibition of the latter was 1:1 (open circle). For comparison, the stoichiometry of interaction of SK Hepatoma TFPI with bovine factor $X_a$ was also 1:1 (closed circle).

Inhibition of Tissue Factor-Induced Coagulation

The ability of the active, refolded E. coli TFPI to inhibit tissue factor-induced coagulation in human plasma was compared with that of the purified SK Hepatoma TFPI. The activity of the E. coli TFPI was approximately two fold more active than SK Hepatoma TFPI on a per mol basis as judged from the concentrations of each TFPI that produce the same prolongation of clotting time.

TABLE 1

Summary of refold and purification of active E. coli TFPI.

| | $A_{280}$ nm | Volume (ml) | Total $A_{280}$ nm | Specific activity[a] (Sk unit/mA) | Yield |
|---|---|---|---|---|---|
| Starting material 0.56 g inclusion body | — | — | — | — | — |
| Sulfonated inclusion body | 6.1 | 25 | 153 | 0 | — |
| HiLoad Q pool | 0.8 | 46 | 37 | 0 | — |
| Refold mixture | 0.035 | 1050 | 37 | 0.66 | 100 |
| Mono S pool | 0.142 | 48 | 6.8 | 2.0 | 18 |

[a]Specific activity was determined by tissue factor-induced coagulation time assay as described in METHODS. One SK unit is defined as the amount of activity equivalent to that produced by 1 mA ($1 \times 10^{-3}$ absorbance unit at 280 nm or 1.31 ug) of purified full-length SK hepatoma TFPI.

Example 2

This example illustrates the effectiveness of using LACI to treat patients susceptible to or afflicted with sepsis. In particular, this example illustrates the effectiveness of using LACI to treat a sepsis-associated coagulation disorder, namely, DIC.

Recombinant TFPI was expressed as a glycosylated protein using mouse C127 cells as host and was purified by chromatography on a monoclonal antibody convalently attached to Sepharose 4B as described by Day et al. [Blood 76, 1538(1990)].

Baboons, 9 month of age weighing 9-13.9 kg, were randomly selected for LACI or excipient pretreatment (1 hr or 15 min) protocol. Each baboon is immobilized with ketamine hydrochloride, 14 mg/kg intramuscularly on the morning of the study and slowly anesthetized with sodium pentobarbital (~9 mg/kg) via a percutaneous catheter positioned in the cephalic vein and brachial vein. The femoral artery and one femoral vein are cannulated aseptically to measure aortic pressure, obtain blood samples, and for infusion of LACI, live organisms, isotonic sodium chloride and sodium pentobarbital. Animals were pretreated with LACI [3.5 mg LACI per ml of excipient (150 mM sodium chloride and 20 mM sodium sulfate)] or excipient control as an I.V. bolus 40 µg/kg over 15 minutes and then as an infusion at 5.6 µg/kg/min for 545 minutes in the left cephalic vein. Baboons were challenged at time 0 with either 3 ml/kg ($4 \times 10^{10}$) or 4 ml/kg ($5 \times 10^{10}$) of live E. coli. The actual dosing schedule and group assignment appear below:

| | # of Animals | | Time of Test Article Administration | Average Bacterial Dose |
|---|---|---|---|---|
| Group | Males | Females | (min.) | (cfu/kg) |
| 1 | 1 | 4 | Excipient −60(3) −15(2) | $4.1 \times 10^{10}$ |
| 2 | 1 | 2 | LACI −60(3) | $3.8 \times 10^{10}$ |
| 3 | 0 | 2 | Excipient −15(2) | $5.4 \times 10^{10}$ |
| 4 | 0 | 3 | LACI −15(3) | $4.9 \times 10^{10}$ |

Blood samples were collected at −60 or −15, 0, +60, +120, +240, +360, +600, and +720 minutes for determination of levels of fibrinogen and fibrin degradation products. Results are shown in Tables 2 and 3.

TABLE 2

Individual Animal Fibrinogen Level (% of Time Zero)

| | −60/−15 | 0 | +60 | +120 | +240 (min.) | +360 (min.) | +720 (min.) |
|---|---|---|---|---|---|---|---|
| Group 1 | 100 | 100 | 100 | 67 | 40 | 23 | 16 |
| | 100 | 100 | 93 | 85 | 16 | 1 | 1 |
| | 100 | 95 | 100 | 68 | 32 | 25 | 15 |
| | 100 | 100 | 100 | 100 | 29 | 8 | 6 |
| | 100 | 100 | 85 | 64 | 52 | 24 | 20 |
| Average | 100.0 | 99.0 | 95.6 | 76.8 | 33.8 | 16.2 | 11.6 |
| STD DEV | 0.0 | 2.0 | 6.0 | 13.7 | 11.9 | 9.8 | 7.0 |
| Group 2 | 100 | 84 | 84 | 64 | 84 | 84 | 84 |
| | 100 | 100 | 86 | 100 | 86 | 108 | 86 |
| | 100 | 83 | 108 | 108 | 100 | 95 | 108 |
| Average | 100.0 | 89.0 | 92.7 | 90.7 | 90.0 | 95.7 | 92.7 |
| STD DEV | 0.0 | 7.8 | 10.9 | 19.1 | 7.1 | 9.8 | 10.9 |
| Group 3 | 100 | 100 | 100 | 100 | 44 | 15 | 8 |
| | 100 | 100 | 100 | 82 | 19 | 7 | 6 |
| Average | 100.0 | 100.0 | 100.0 | 91.0 | 31.5 | 11.0 | 7.0 |
| STD DEV | 0.0 | 0.0 | 0.0 | 9.0 | 12.5 | 4.0 | 1.0 |
| Group 4 | 100 | 100 | 121 | 121 | 100 | 100 | 83 |
| | 100 | 90 | 90 | 85 | 79 | 62 | 60 |
| | 100 | 80 | 91 | 80 | 72 | 75 | 64 |
| Average | 100.0 | 90.0 | 100.7 | 95.3 | 83.7 | 79.0 | 69.0 |
| STD DEV | 0.0 | 8.2 | 14.4 | 18.3 | 11.9 | 15.8 | 10.0 |

Group 1 = Excipient control ($4.1 \times 10^{10}$ cfu/kg)
Group 2 = LACI ($3.8 \times 10^{10}$ cfu/kg)
Group 3 = Excipient control ($5.4 \times 10^{10}$ cfu/kg)
Group 4 = LACI ($4.9 \times 10^{10}$ cfu/kg)

TABLE 3

Individual Animal Fibrin Degradation Products (µg/ml)

| | −60/−15 | +240 (min.) | +720 (min.) |
|---|---|---|---|
| Group 1 | 10.00 | 320.00 | 320.00 |
| | 10.00 | 80.00 | 320.00 |
| | 10.00 | 80.00 | 160.00 |
| | 10.00 | 80.00 | 160.00 |
| | 10.00 | 10.00 | 160.00 |
| Average | 10.00 | 114.00 | 224.00 |
| STD DEV | 0.00 | 106.51 | 78.38 |
| Group 2 | 10.00 | 10.00 | 10.00 |
| | 10.00 | 10.00 | 10.00 |
| | 10.00 | 10.00 | 10.00 |
| Average | 10.00 | 10.00 | 10.00 |
| STD DEV | 0.00 | 0.00 | 0.00 |
| Group 3 | 10.00 | 40.00 | 160.00 |
| | 10.00 | 20.00 | 160.00 |
| Average | 10.00 | 30.00 | 160.00 |
| STD DEV | 0.00 | 10.00 | 0.00 |
| Group 4 | 10.00 | 10.00 | 20.00 |
| | 10.00 | 10.00 | 80.00 |
| | 10.00 | 20.00 | 40.00 |

TABLE 3-continued

Individual Animal Fibrin Degradation Products (μg/ml)

|  | −60/−15 | +240 (min.) | +720 (min.) |
|---|---|---|---|
| Average | 10.00 | 13.33 | 46.67 |
| STD DEV | 0.00 | 4.71 | 24.94 |

Group 1 = Excipient control (4.1 × $10^{10}$ cfu/kg)
Group 2 = LACI (3.8 × $10^{10}$ cfu/kg)
Group 3 = Excipient control (5.4 × $10^{10}$ cfu/kg)
Group 4 = LACI (4.9 × $10^{10}$ cfu/kg)

There was a clear effect by LACI on fibrinogen levels in the E. coli treated animals. A drop in fibrinogen is prominent in the excipient controls (Groups 1 and 3) from 240 minutes (i.e., two hours after the end of bacterial infusion) and on. The drop was substantially prevented by LACI pretreatment when the baboons were challenged with lower dose bacteria (Group 2), and attenuated when the animals are challenged with the higher dose bacteria (Group 4).

The generation of fibrin degradation products was not detectable in Group 2, and slowed down and reduced in Group 4 animals as a result of pretreatment with LACI. The differences in the above coagulation parameters among the groups are not as prominent at 720 minutes possibly due to the fact that the LACI infusion was stopped at 540 minutes and that a certain circulating level of LACI may be necessary to maintain an effect.

In addition to the above analyses, histopathology studies wherein tissues of all groups of the above baboons were processed, stained with hematoxylin and eosin, and examined by light microscopy. The kidneys, lungs, adrenals, liver and spleen appeared to be the main organs affected by the E. coli challenge. Reduced pathology in some target organs such as adrenals and kidneys was observed.

Thus, the conclusion drawn from the above is that the effect of LACI on septic shock is evident, particularly in view of the attenuation of the fibrinogen drop end generation of fibrin degradation products, and the reduced pathology in some target organs, such as the adrenal and kidney.

Example 3

This example illustrates the effectiveness of using LACI to promote survival in patients which are susceptible to or afflicted with sepsis. In particular, this example illustrates the effectiveness of using LACI to treat gran-negative sepsis. LACI was prepared by the method described above in Example 1.

Male and female Papio anubis baboons (7.6±2.4 kg) from the Charles River Primate Center (Wilmington, Mass.) were quarantined for a minimum of thirty days in the University of Oklahoma Animal Facility (Oklahoma City, Okla.).

Each baboon was immobilized with ketamine hydrochloride, 14 mg/kg intramuscularly on the morning of the study and slowly anesthetized with sodium pentobarbital (~9 mg/kg) via a percutaneous catheter positioned in the cephalic vein. To compensate for insensible fluid loss, the animals were infused with isotonic saline at a rate of 3.3 ml/kg/hr for 12 hours via the barachial vein in the right leg. LACI or PBS buffer control was administered to the animals through the brachial vein 30 minutes after the administration of bacteria. LACI was administered at a loading dose over fifteen minutes and simultaneously started a continuous infusion of LACI for an additional 675 minutes (counting from start of bacterial infusion, which was defined as time zero).

E. coli 086: K61H were used to inoculate tryptic soy broth agar (2); viability counts of the inoculum were determined by standard dilution techniques. At time zero, baboons received an infusion of 4.5×$10^{10}$ live bacteria per kg body weight (4 mls/kg), administered through a percutaneous catheter in the right cephalic vein by continuous infusion for 2 hours.

The femoral artery and one femoral vein were cannulated aseptically to measure mean systemic arterial pressure, obtain blood samples and for antibiotic administration. Gentamicin was given (9 mg/kg i.v.) at end of E. coli infusion, i.e., at T+120 min. for 30 minutes and then 4.5 mg/kg at T+300 min. and T+540 minutes for 30 min. Gentamicin (4.5 mg/kg IM) was then given at the end of the experiment and once daily for 3 days.

Animals were maintained under anesthesia and monitored continuously for 12 hours. Blood samples were collected hourly for hematology, clinical chemistry, cytokines (TNF, IL-6) and LACI determinations. Similarly, respiration rate, heart rate, mean systemic arterial pressure and temperature were monitored hourly.

Animals surviving 7 days were considered survivors and subsequently euthanized for necropsy at the 8th day.

See Hinshaw, L. B., Archer, L. T., Beller-Todd, B. K., Coalson, J. J., Flournoy, D. J., Passey, R., Benjamin, B., White, G. L. Survival of primates in $LD_{100}$ septic shock following steriod/antibiotic therapy, J. Surg. Res., 26, 151-170 (1989), and Hinshaw, L. B., Brackett, D. J., Archer, L. T., Beller, B. K., Wilson, M. F. Detection of the "hyperdynamic state" of sepsis in the baboon during lethal E. coli infusion, J. Trauma, 23, 361-365, (1982); which are incorporated herein by reference.

Results of this study are shown in Table 4.

TABLE 4

E. coli LACI Baboon Data

| Baboon # | Fibrinogen 240' % of T = O | Fibrinogen 720' % of T = O | Platelet Ct. 702' % of T = O | Hemolysis 6 hr | Hemolysis 12 hr | Blood Pressure 3 hr % of T = O | Blood Pressure 12 hr | Consciousness | Recovery at 24 hr. Alertness | Recovery at 24 hr. Mobility | Survival Time |
|---|---|---|---|---|---|---|---|---|---|---|---|
| Controls |  |  |  |  |  |  |  |  |  |  |  |
| 3 | <1 | <1 | 27 | -- | -- | 61 | 41 |  |  |  | 18 hrs |
| 6 | 8 | <1 | 21 | — | — | 51 | 84 | -- | -- | -- | 33½ hrs |
| 18 | 4 | <1 | 19 | — | — | 65 | 84 | — | — | — | 66 hrs |

TABLE 4-continued

E. coli LACI Baboon Data

| Baboon # | Fibrinogen 240' % of T = O | 720' % of T = O | Platelet Ct. 702' % of T = O | Hemolysis 6 hr | 12 hr | Blood Pressure 3 hr % of T = O | 12 hr | Consciousness | Recovery at 24 hr. Alertness | Mobility | Survival Time |
|---|---|---|---|---|---|---|---|---|---|---|---|
| 19 | <1 | <1 | 22 | -- | -- | 89 | 122 | – | – | – | 7 days |
| 20 | 4 | <1 | 26 | + | + | 53 | 45 | – | – | – | 83 hrs |
| Low Dose (Loading Dose 0.7 mg/kg: Maintenance Dose 3.0 ug/kg/min) | | | | | | | | | | | |
| 7 | 78 | 8 | 37.5 | – | -- | 62 | 50 | | | | 18 hrs |
| 8 | 55 | 50 | 32.2 | – | – | 38 | 69 | ++ | ++ | ++ | 53 hrs |
| 10 | 32 | 10 | 15 | – | – | 73 | 63 | + | + | – | 7 days |
| 11 | 93 | 83 | 26 | + | + | 63 | 89 | ++ | ++ | – | 7 days |
| 16 | 43 | 43 | 33 | – | – | 75 | 80 | – | – | – | 7 days |
| 17 | 74 | 84 | 30 | + | + | 75 | 90 | ++ | + | + | 7 days |
| High Dose (Loading Dose 1.0 mg/kg: Maintenance Dose 9.5 up/kg/min) | | | | | | | | | | | |
| 4 | 77 | 22 | 70 | + | + | 56 | 87 | + | + | + | 7 days |
| 5 | 79 | 113 | 59 | + | + | 75 | 77 | ++ | ++ | ++ | 7 days |
| 12 | 116 | 71 | 48 | + | + | 79 | 68 | ++ | ++ | ++ | 59.5 hrs |
| 13 | 86 | 49 | 30 | + | + | 61 | 82 | ++ | ++ | ++ | 7 days |
| 14 | 88 | 105 | 30 | + | + | 74 | 71 | ++ | ++ | ++ | 7 days |
| 15 | 54 | 54 | 41 | + | + | 78 | 90 | ++ | ++ | ++ | 7 days |

Recovery Code
++ Very alert, very mobile
+ Somewhat alert, slightly mobile
– Appears tired, cognizant of surrounding, sitting up, petechia noted
-- Lying down, not cognizant of surroundings, eyes blinking, petechia noted
Hemolysis Code
– Hemolysis noted
+ No hemoylsis noted Example 4

Production of LACI

A. Aged Cells

Human umbilical vein endothelial cells (HuVec) were plated and maintained in a standard tissue culture medium. They were aged for 32-36 days, fed twice a week with fresh medium, and the medium supernatant was removed after 32 days (called conditioned medium or CM). The CM contained LACI.

B. Induced Cells

The same HuVec cells were plated and maintained in a tissue culture medium for 24-48 hours and then they were contacted with various concentrations of tumor necrosis factor (TNF) for 3-4 days. The medium containing LACI was removed and is called TNF CM.

Example 5

LACI Inhibition of Sepsis

The following assay was devised to measure the inhibition of sepsis by LACI. HuVec cells were plated and incubated for 48 hours. Bacterial lipopolysaccharide (LPS) was added as an inducer of sepsis. The addition of LPS was the best way to stimulate a sepsis-like response which was broader than simple coagulation. When the inducer was added, a test sample was added to examine its effect on the LPS effect on the endothelial cells. The sample that was tested contained LACI. The cells were incubated between 4 and 5 hours and then chromozyme was added. The chromozyme contains Factors II, VII, IX, and X. This first method measured the inhibition of tissue factor induction and inhibition of activity. In an alternative of the present assay, which measures inhibition of tissue factor activity, the sample was added together with the chromozyme and then incubated for 45 minutes. LACI inhibitory activity was measured by reading optical density (due to color changes) in a spectrophotometer at $A_{405}$.

Figure 2:
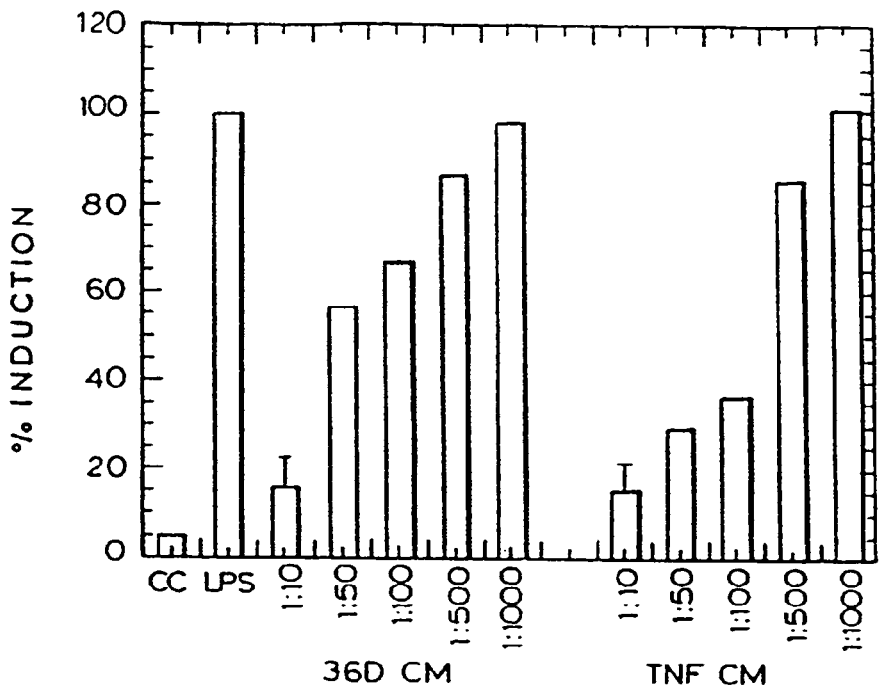
FIG. 2 shows the inhibition of tissue factor activity by 36 day conditioned medium (CM) and TNF induced CM.
Figure 3:
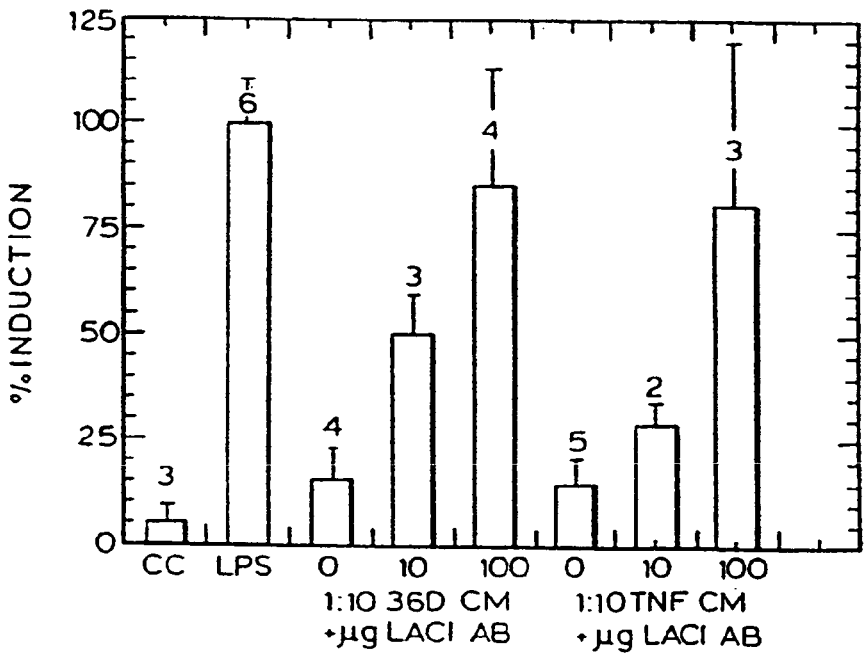
FIG. 3 shows LACI neutralization of CM from endothelial cells.

Aged and TNF induced condition medium was prepared as in Example 4. FIG. 2 displays a dose dependent inhibition of tissue factor activity by a substance contained in the respective media shown in the figure. The nature of the substance was identified by the following experiment which involved inhibition of tissue factor activity determined as follows: HuVec cells were prepared for the assay. One cell sample was left untreated as a control. Another cell sample was induced with LPS without the addition of any potential inhibitor. Subsequently, six classes of samples were run using aged and TNF condition medium containing LACI with 0, 10, and 100 mg of LACI antibody. FIG. 3 shows the result of this experiment. For example, (Lane 1 starting from the left) was the control and very little tissue factor activity was detected. Lane 2 shows 100% of tissue factor activity and induction by addition of LPS. Lanes 3, 4, and 5 show linearly increasing amounts of activity (and thus induction) depending on the amount of anti-LACI antibody. For example, the 0 concentration (Lane 3) showed that very little tissue factor activity was detectable, suggesting lack of tissue factor induction. This indicated that LACI inhibited the activity of the tissue factor induced by LPS. Lanes 4 and 5 show a similar result, however, the amount of tissue factor activity/induction increased as larger amounts of LACI were neutralized by the anti-LACI antibody. Lanes 6, 7, and 8 (with TNF conditioned medium) also display a nearly identical magnitude of inhibition of tissue factor activity as that shown for Lanes 3, 4, and 5. To confirm the identity of the substance in the conditioned media, we used various concentrations of highly purified LACI in the absence or presence of neutralizing antibodies.

Figure 4:
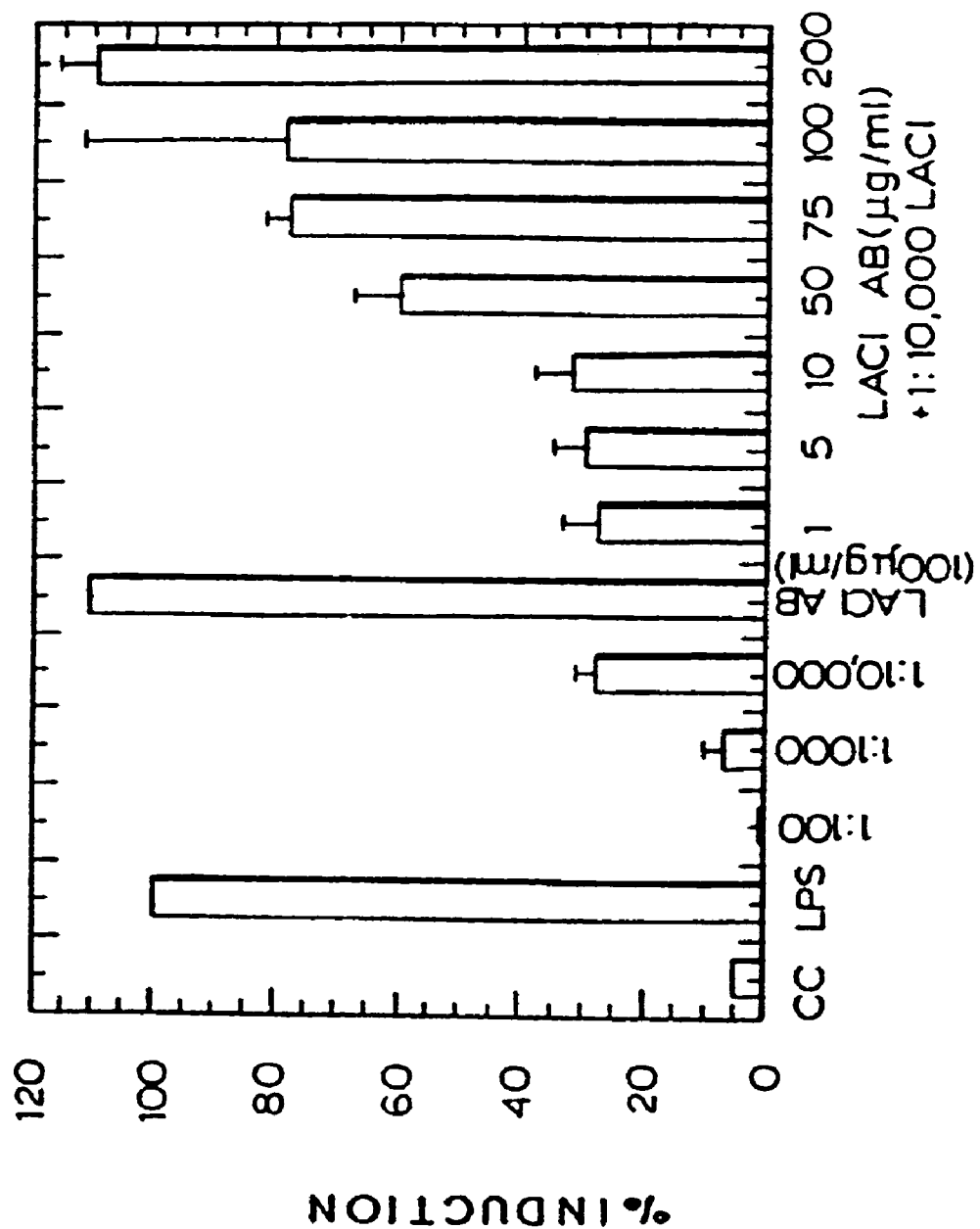
FIG. 4 shows antibody neutralization of LACI protein.

The results match the findings utilizing aged and TNF induced conditioned media. See FIG. 4.

These data indicate that LACI will inhibit the effects of LPS on HuVec cells in a concentration dependent manner and this effect may be reversed upon the addition of various concentrations of neutralizing antibodies to LACI. Furthermore, this model proves that LACI can be used to treat sepsis, and its effects were not simply restricted to its anticoagulant properties.

Example 6

Treatment of Human Patients Using LACI

Human patients which are affected by sepsis may be therapeutically treated by using LACI. When the patient presents themselves with increased temperature, drop in blood pressure, a decrease in white cell count, and a drop ≧20% in fibrinogen, LACI is administered intravenously as a bolus dose of 3-10 mg/kg and as an infusion of 10-20 µg/kg/min for 3-4 hours. Alternatively, LACI may be administered at a continuous rate of approximately 10 mg/kg/min for 3 days or for 4 hours daily for 3-4 days. Antimicrobial therapy or broad spectrum antibiotics are administered to the patient along with the LACI.

LACI is given prophylactically in the same manner.

Example 7

In this experiment, highly purified recombinant LACI (6 mg/kg) was administered either thirty minutes or four hours after the start of a lethal intravenous *E. coli* infusion in baboons. Early post treatment of LACI resulted in a) permanent 7 day survivors (5/5) with significant improvement in quality of life, while the mean survival time for the controls (5/5) was 39.9 hrs. (no survivors); b) significant attenuations of the coagulation response and various measures of cell injury, with significant reductions in pathology observed in *E. coli* sepsis target organs including kidneys, adrenals and lungs. LACI administration did not affect the drop in mean systemic arterial pressure, the increases in respiration and heart rate or temperature changes associated with the bacterial infusion. LACI treated *E. coil* infected baboons had twenty fold lower IL-6 levels than their phosphate buffered saline treated controls. In contrast to the earlier 30 minute treatment, the administration of LACI at four hours i.e., 240 minutes, after the start of bacterial infusion resulted in prolongation of survival time, with forty percent improvement in survival rate (two survivors) and some attenuation of the coagulopathic response, especially in animals in which fibrinogen levels were above 10% of normal at the time of LACI administration.

Recombinant Tissue Factor Pathway Inhibitor

LACI was expressed in the human hepatoma cell line SK Hep as described in Wun et al. 1992, *Thrombosis Haemost.*, 68:54-59. Detection of Bacterial Endotoxins with the Limulus Amebocyte Lysate Test, Alan R. Liss, Inc., NY. The material was purified by standard techniques to provide >95% pure preparations. LACI was formulated in 150 mM NaCl and 20 mM NaPO$_4$ (pH 7.2), which served as the excipient control. Final protein concentration in a LACI sample ranged from 2.3-3.7 mg/ml, determined by amino acid composition; endotoxin levels ranged from 8 to 27 endotoxin units per 15 milligrams of protein. LACI lots were monitored for biological activity using a tissue factor inhibition assay (Boze et al., *Blood* 71:335-343 (1988)).

Baboons

Male and female Papio anubis baboons (7.6±2.4 kg) from the Charles River Primate Center (Wilmington, Mass.) were quarantined for a minimum of thirty days in the University of Oklahoma Health Sciences Center Animal Resource Facility (Oklahoma City, Okla.). Animals were free of infections or parasites with hematocrits ≧36%.

Bacteria

*Escherichia coli* 086:K61H organisms (ATCC 33985; Rockville, Md.) were isolated from a stool specimen at Children's Memorial Hospital, Oklahoma City. They were stored in the lyophilized state at 4° C. after growth in tryptic soybean agar and reconstituted and characterized as described in Hinshaw et al., *J. Trauma* 23:361-365 (1982).

Assays

Endotoxin Measurement

Endotoxin levels in LACI preparations and the excipient buffer were monitored by the limulus amebocyte lysate test (Wun et al., *Thromb. Haemost.* 68:54-59 (1992)). LPS from *E. coli* (B5505; Mallinckrodt, St. Louis, Mo.) were included as a standard. The detection limit of the assay was 10 endotoxin units (E.U.)/ml.

TNF ELISA

Baboon TNF levels in plasma were measured using an ELISA developed for detecting human TNF (Creasey et al., *Circ. Shock* 33:84-91 (1991)): a purified monoclonal anti-TNF antibody (24510E11) was bound to microtiter plate wells (Dynatech Immunolon I, Fisher). Unoccupied binding sites on the plastic were then blocked with bovine serum albumin (BSA). Aliquots of standard concentrations of purified recombinant human TNF or baboon plasma samples were incubated in duplicate. ELISA wells were exposed to horseradish peroxidase (HRP)-conjugated affinity packed polyclonal rabbit antibody to recombinant human TNF followed by 0-phenylenediamine substrate as chromogen. Wells were rinsed repeatedly with phosphate-buffered saline solution (PBS, Ph 7.5) between successive incubations. Optical density (OD) was read on an automated dual-wavelength plate reader at 490 nm (Bio-Tek Instruments). The detection limit for baboon TNF in this assay was 0.5 ng/ml.

IL-6 Bioassay

IL-6 bioactivity was quantified in baboon plasma using the IL-6-dependent murine hybridoma cell line B9, using IL-6 commercially available from Amgen, Inc. (Thousand Oaks, Calif.), as the assay standard (Creasey et al., supra). The detection limits of this assay were 10 pg/ml.

LACI Levels

A competitive fluorescent immunoassay for LACI was used as previously described in Novotny et al., *Blood* 78:394-400 (1991): a rabbit anti-LACI IgG was used to capture LACI in the sample to be tested and FITC-LACI (HepG2) was added to quantitate the number of anti-LACI binding sites remaining. Standard curves were constructed using dilutions of pooled human plasma (George King Biomedical, Overland Park, Kans.) or of pure HepG2 LACI.

The LACI functional assay (tissue factor-inhibition assay) is a three-stage clotting assay. Briefly, in the first stage, the sample to be tested is incubated with crude brain tissue factor, factor X, factor VII, and calcium. After 30 minutes of incubation, additional factor X is added and 1 minute later factor X-deficient plasma is added and time to clot is measured in a fibrometer. Residual factor VII(a)/tissue factor activity in the second stage of the assay is inversely proportional to the LACI concentration in the test sample. Thus, prolongation of the clotting time reflects higher LACI activity. Standard curves were constructed using dilutions of pure HepG2 LACI.

Pharmacokinetic Analysis

The data for each baboon (µg LACI/ml plasma at various sample times) were fit to a two-compartment model. The model parameters were determined by nonlinear least squares curve-fitting procedures using the PKDAAS data analysis system (developed for the VAX computer at Chiron Corporation deposited at the U.S. Copyright Office as registration No. TXU 416-977). Corrected concentrations at each time, C(t), were weighted as the reciprocals of each concentration squared. The weighted values were then fitted to individual subjects' curves using the following biexponential equation:

$$C(t)=(DOSE/VC)*[(1-B)*2^{-t/\alpha}+B*2^{-t/\beta}],$$

where t is time and VC, B, α, and β are model parameters. The sum of the coefficients was normalized to 1.0. The systemic clearance (CL) was then calculated from:

$$CL=VC/MRT, \text{ where}$$

$$MRT=[(1-B)*\alpha+B*\beta]\ln(2).$$

Statistical Analysis

Data were analyzed with the students' t-test to determine significant differences (p<0.05) in means between groups at given times. The analysis of variance (ANOVA) and the multicomparison Duncan's test were used to determine significant differences between means at time 0 and subsequent times within groups. The Fisher's exact test was used to determine significant differences between groups with respect to survival rates.

Pharmacokinetic Studies

To establish the appropriate LACI dosage for the E. coli septic shock model, we performed a pharmacokinetic study in three healthy baboons. FIG. 5 shows that administered as a bolus at 0.5 mg/kg, LACI exhibited a two phase half life; an alpha phase of approximately two minutes and a beta phase of about two hours. These data were then modeled as described above to identify the necessary LACI dosage to achieve a circulating LACI serum concentration of 2 µg/ml, which was arbitrarily defined as the desired LACI blood concentration since it has been reported that endogenous levels of LACI in primates is approximately 0.1 µg/ml (Novotny et al., J. Biol. Chem. 264:18832-18837 (1989)). Thus to achieve a 20-fold increase in LACI serum concentrations in the baboons, we administered LACI at a loading dose of 700 µg/kg and a maintenance dose of 10 µg/kg/min (i.e. a total dose of 6,000 µg/kg) started simultaneously, 30 minutes after the start of the E. coli infusion.

Experimental and Infusion Procedures

Each baboon was immobilized with ketamine hydrochloride, 14 mg/kg intramuscularly on the morning of the study and slowly anesthetized with sodium pentobarbital (~9 mg/kg) via a percutaneous catheter positioned in the cephalic vein as described in Hinshaw et al., J. Surg. Res. 28:151-170 (1989). To compensate for insensible fluid loss, animals were infused with isotonic saline at 3.3 ml/kg/hr for 12 hours via the brachial vein 30 minutes or 240 minutes, respectively, after the administration of bacteria. LACI was administered at a loading dose of 700 µg/kg for 15 minutes and a continuous infusion of LACI at 10 µg/kg/min was given for an additional 525 minutes (counting from start of bacterial infusion, which was defined as time zero). To deliver the same total LACI dose per baboon, animals treated at +240 minutes received a loading dose of 2.8 µg/kg for fifteen minutes and simultaneously received a continuous infusion of LACI at 10 µg/kg/min for 480 min.

E. coil 086:K61H were used to inoculate tryptic soy broth agar, and viability counts of the inoculum were determined by standard dilution techniques. At time zero, baboons received an infusion of $\geq 4.5 \times 10^{10}$ live bacteria per kg body weight (4 ml/kg), administered through a percutaneous catheter in the right cephalic vein by continuous infusion for 2 hours.

The femoral artery and one femoral vein were cannulated aseptically to measure mean systemic arterial pressure, obtain blood samples and for antibiotic administration. Gentamicin was given (9 mg/kg i.v.) at the end of E. coli infusion, i.e., at T+120 for 30 minutes and then 4.5 mg/kg at T+360 and T+540 minutes for 30 min. Gentamicin (4.5 mg/kg IM) was then given at the end of the experiment and once daily for 3 days.

Animals were maintained under anesthesia and monitored continuously for 12 hours. Blood samples were collected hourly for hematology, clinical chemistry, cytokines (TNF, IL-6, and LACI determinations. Similarly, respiration rate, heart rate, mean systemic arterial pressure and temperature were monitored hourly. Animals were continuously observed for the first 30 hours of the experiment. Those surviving 7 days were considered permanent survivors and were subsequently euthanized with sodium pentobarbital for necropsy at the 8th day.

Ten baboons (5 LACI treated and 5 excipient controls) were intravenously administered 2 hour lethal infusions of E. coli. Table 5 shows that LACI rescued five of five E. coli treated baboons who became permanent survivors. The mean E. coli dosage of the LACI treated was $5.7 \times 10^{10}$ CFU/kg and all animals survived more than 7 days. The mean E. coli dosage of the excipient control group was $5.5 \times 10^{10}$ CFU/kg and the mean survival was 39.9 hours (Table 5). The mean weight of the excipient control group was 8.4 kg (range 5.9 to 12.1 kg) and that of the LACI treated was 6.8 kg (range 5.2 to 8.0 kg). Two females and three males composed the excipient control group, while the LACI treated group consisted of five males. There was no difference in the mean dose of E. coli administered to each group (p>0.05) nor in the animals' weights (p>0.05).

LACI treated baboons moved about the cage energetically, consumed some food and drank water normally within 24 hours of receiving lethal E. coli ($LD_{100}$). The excipient control baboons, however, were very lethargic, appeared to have difficulty breathing and exhibited multiple petechiae over their bodies indicating the occurrence of DIC in the dermal microvasculature.

Coagulation and Hematological Responses to LACI Administration at +30 Minutes

To determine the mechanism by which LACI protected the bacterially infected baboons we measured selected physiologic parameters associated with coagulation, clinical chemistries and the inflammatory response. FIG. 6 shows that many of the coagulopathies associated with the bacterial infection were inhibited and/or attenuated in the LACI treated baboons. Fibrinogen levels in excipient control animals dropped by approximately 80% by 3 hours, while the LACI treated baboons experienced only a 20% drop (p<0.0001). Similarly, the rise in fibrin degradation products at 240 and 720 minutes, as a marker of fibrinogen consumption, was not evident in the LACI treated animals as compared to the controls (p<0.05).

Activated partial thromboplastin time (APTT) and prothrombin time (PT) were extremely prolonged at times beyond four hours in the excipient controls (FIG. 6). APTT increased from 37 to 208 and then to 226 seconds while PIT increased from 14 to 58 and then to 137 seconds, at four and 12 hours, respectively. In contrast, APT increased from 32 to 45 to 60 seconds at four and 12 hours, respectively, and PT increased from 15 to 18 seconds to 22 seconds at four and 12 hours, respectively, in the LACI treated baboons (p<0.05).

A gradual drop in platelet cell concentration was noted in the excipient controls and in the LACI treated baboons over the 12 hour observation period (FIG. 6). LACI treatment, however, retards the drop and is most apparent at $\geqq 4$ hours. The mean platelet concentration of the control group at four, six and twelve hours were 102.8±26, 69±20 and 43±5.0. In contrast, the mean platelet concentration of the LACI treated group at the same times were 249±44, 236±35, and 153±31, respectively.

Despite the lack of visible hemolysis in the LACI treated plasma samples, the hematocrit decreased with time and was lower at 12 hours in the experimental (treated) group, 36±2%, as compared to the control group, 44±2.% (p<0.05). Furthermore, the mean 7 day hematocrit value of the survivors was also low as compared to baseline: 28±1% versus 42±0%.

Consistent with the hematocrit results the red blood cell concentration dropped only slightly over the initial 12 hours in both the control (4.94±21 to 4.4±0.11) and LACI treated groups (5.20±0.10 to 4.88±0.17), and a low (3.42±0.2×10$^6$) red cell concentration was observed in the survivors.

Leukopenia occurred to the same degree in the LACI treated and control group, the lowest values (~1.48×10$^3$/μl) recorded at 2 hours; however, the white blood cell concentration was found elevated at 7 days in the survivors with a mean of 19.2±3.5 as compared to the base line of 9.0±1.5×10$^3$/μl.

Clinical Responses to LACI Administration at +30 Minutes

Respiration and heart rate increased in both groups. Respiration rate rose quickly after the start of the bacterial infusion and remained elevated for the 12 hour period. Similarly, heart rate increased dramatically, from 120 beats/min to 200 beats/min, within the first two hours of *E. coli* infusion and remained elevated during the 12 hours.

Mean systolic arterial pressure (MSAP) and temperature equally declined in the LACI treated and control groups. A dramatic decrease in MSAP was observed at the end of the bacterial infusion. MSAP declined from 107±5 mm Hg to 69±5 at two hours and then gradually returned to 93±11 by 10 to 12 hours in the control group. Similarly, MSAP declined from 115±9 to 74±3 at 2 hours and rose to 85±7 from 6 hours on to 12 hours. The ten baboons had a decreased temperature response to the *E. coli* infusion. The mean excipient control temperature at the start of the experiment was 37.3±0.1° C. and declined slowly to 34.7±2.2° C. at 12 hours. The mean LACI treated temperature was initially 37.0±0.3° C. and changed minimally over the 12 hours where it was 36.9±0.2° C.

Blood Chemistries

Table 6 summarizes clinical chemistries of the *E. coli* infected and treated ten baboons. Increases in serum creatinine, total bilirubin, uric acid, lactic acid, triglycerides, anion gap, chloride and sodium were measured at 12 hours. The magnitude of the increases, however, was lower in the LACI treated animals than the excipient controls (p<0.05). Changes in the concentrations of the following parameters were observed: albumin, alkaline phosphatase, AST, BUN, calcium, cholesterol, CK, carbon dioxide, cortisol, potassium, lactic dehydrogenase, phosphorous, SGPT and total protein. Their increases or decreases in concentration were not affected by the LACI treatment (p>0.05). However, the mean concentrations of albumin, urea nitrogen (BUN) and lactate did not return to baseline values in the LACI treated animals (i.e. the survivors) at 7 days. Specifically, albumin concentrations were 2.7±0.2 at 7 days as compared to 3.7±0.1 at the start of the experiments. Thus albumin was reduced by about 25%. Similarly, serum values of urea nitrogen (BUN) at 7 days was 13.8±2.1 versus 29.6±3.9 at the beginning of the experiment. Finally, lactate concentrations were increased by about 3-fold in the survivors. The mean baseline lactate concentrations of these animals was 1.7±0.5 meq/L at the start of the procedure and increased to 5.7±1.2 meq/L at 7 days.

Increases in glucose concentration were observed within two hours in both groups (p<0.05). Mean values fell gradually beyond the initial increase but remained consistently higher in the LACI treated animals (p<0.05) until 12 hours. Increases in arterial pH occurred in both groups.

TNF and IL-6 Levels

Plasma TNF concentrations were elevated in both the excipient group and LACI treated baboons. Consistent with our previous studies (Creasey et al., *Circ. Shock* (1991) 33:84-91), peak TNF levels were at 120 min, i.e. at the end of *E. coli* infusion. LACI treatment did not appear to affect the rise in serum TNF concentrations nor the kinetics of its release (Table 7). Plasma IL-6 concentrations also increased with time in the excipient control group. where IL-6 levels started at 26-39 picograms and rose to 100-200 nanograms beyond four hours (Table 8). Interestingly, plasma IL-6 concentrations in the LACI treated animals were lower than those of the control group, especially at and beyond four hours. IL-6 concentrations were about 20-fold lower in the LACI treated than the excipient controls at 12 hours (p<0.05).

Administration of LACI at +240 Minutes

To determine the time beyond which LACI may no longer be effective in attenuating the *E. coli* shock, we delayed the administration of LACI to two hours after the end of the bacterial infusion. Fibrinogen consumption and the generation of fibrin degradation products were to be clearly evident at four hours. Table 8 shows that the mean *E. coli* dosage of the excipient control group in this series of experiments was 5.68 (±2.6)×10$^{10}$ CFU/kg and the mean survival time of 28.2±9.6 hours. The mean *E. coli* dosage of the LACI group was 5.43 (±0.19)×10$^{10}$ CFU/kg and the mean survival time of 99±29 hours. Two of the five LACI treated animals were 7 day survivors (p<0.05). There was no difference in the mean weight or *E. coli* dosage administered to each of the above groups (p>0.05).

Biological and Biochemical Effects of Administration of LACI at +240 Minutes

The administration of LACI two hours after the end of the two hour bacterial infusion was effective in slightly attenuating the coagulopathic response as evident by decreases in FDP levels, and prothrombin time at $\geqq 12$ hours. Consistent with +30 minutes, IL-6 levels were two-fold lower in the LACI treated baboons than their excipient counterparts at 12 hours. No significant differences in fibrinogen concentrations, APTT and platelet cell concentration were noted at 12 hours between the excipient control and the LACI treated baboons. However, fibrinogen levels at day 7 in the two animals that survived were slightly elevated; FDP, APTT and PT values were back close to normal while platelet cell concentrations were normal in one (435) and lower in the other (97).

Although the red blood cell count and hematocrit fluctuated slightly over time in both groups during the first 12 hours, the two survivors had lower hematocrits at day 7 (35 and 19%) as compared to the start of the procedure (43 and 41%). Similarly, red blood cell concentration was 4.0 and 2.7×10$^6$/mm$^3$ on day 7 versus 4.7 and 4.5×10$^6$/mm$^3$ at day 0.

Clinical chemistries were measured for the ten baboons comprising the plus four hour study as we had performed for the plus thirty minute study. We observed minimal differences between the excipient control and LACI treated baboons at twelve hours. However, consistent with the plus 30 minute study, lactate levels were higher in the LACI treated than the controls (p<0.05) at 12 hours and remained elevated in the two that survived 7 days (13.2 and 4.0 mg/dl versus 0.5 and 0.6 mg/dl at time 0). In contrast, uric acid levels were slightly lower in the LACI treated group than the controls at 12 hours and returned to normal levels in the two LACI treated survivors.

Similar to the plus 30 minute study, all the animals treated at 240 minutes experienced leukopenia, and a gradual but small rise in WBC count over the twelve hours. Furthermore, the two 7 day surviving LACI treated baboons had elevated WBC counts (12.5 and $21.8 \times 10^3$ cells/mm$^3$) at day 7 as compared to 5.1 and $8.0 \times 10^3$ cells/mm$^3$ at time zero; this trend is similar to that observed in the survivors of the baboons treated at +30 minutes with LACI.

Pathological Results

Post-mortem examinations were conducted on all baboons. Surveillance of animals was continuous for the first 36 hours; consequently tissues were removed for analysis within minutes after death thereby avoiding post-mortem autolytic changes. Lungs, liver, adrenals, kidneys, spleen, and gall bladder were target organs of the *E. coli* bacterial infusion. Specifically, animals that received excipient +*E. coli* suffered from severe congestion, hemorrhage, fibrin deposition, edema and massive accumulation of leukocytes in the lungs and liver, severe congestion of medullary sinusoids in the spleen and significant evidence of tubular necrosis and thrombosis within the kidneys and severe cortical congestion in the adrenals. Organs not affected by *E. coli* were stomach, heart, pancreas and small and large intestines. LACI protected the liver, adrenals, kidneys, spleen and gall bladder in which only mild to no pathology were observed. The degree of protection was slightly diminished in the lungs, in which moderate vascular congestion, and mild leukocyte accumulation were observed.

Results from the present study demonstrated that LACI rescued one hundred percent of the baboons given LD$_{100}$ doses of *E. coil* when administered thirty minutes after the start of the bacterial infusion when more than $1 \times 10^{10}$ organisms/kg had already been introduced into the blood of the baboons. In addition, LACI rescued forty percent of the baboons when given two hours after the end of the bacterial infusion i.e. when greater than $5 \times 10^{10}$ organisms/kg had been infused and many of the baboons' host defense mechanisms had been triggered for two hours.

TNF levels peaked at the end of the *E. coli* infusion i.e. at two hours, while IL-1β and IL-6 levels started to appear (Creasey et al., *Circ. Shock* 33:84-91 (1991)); the decline and consumption of fibrinogen and generation of fibrin degradation products become more easily detectable between three and four hours (De Boer, J. P. et al., *Circ. Shock* (In press 1992)). This study shows that LACI could prevent, slow down and even reverse the consumption of fibrinogen, when administered as late as four hours after the start of a lethal bacterial infusion.

In addition to attenuating coagulation, LACI attenuated the degree of cell injury (creatinine, uric acid, lactic acid) and metabolic acidosis (anion gap, chloride and sodium) so clearly evident in the controls. Consistent with the decreased serum levels of many of these markers of hypoxia, acidosis and cell injury, LACI afforded remarkable morphological protection to kidneys, adrenals, liver, spleen and the lungs from pathological changes. The efficacy of LACI in baboons challenged with lethal *E. coli* shows gram-negative shock is an acute inflammatory disease of the vascular endothelium and that significant benefit is achieved by transiently protecting the endothelium from insults associated with gram-negative bacteria.

Previous studies have shown that within the first 30 minutes of the bacterial infusion, the PMN leukocyte concentration in circulating blood fell sharply Taylor et al., *Colloquium Mosbach Molecular Aspects of Inflammation* (1991) Springer Verlag, Berlin Heidelberg, pp. 277-288), thrombin-antithrombin (TAT) complexes, tissue plasminogen activator/plasminogen activator inhibitor (t-PA/PAI) and plasmin anti plasmin (PAP) complexes had started to appear (De Boer, J. P. et al., *Circ. Shock* (1992) In press), and the activation of the complement cascade in lethal *E. coli* challenge was clearly evident (De Boer, J. P. et al., submitted). LACI treatment resulted in the prevention of tubular necrosis and glomerular thrombosis in the kidneys; cortical congestion, hemorrhage, necrosis and leukocyte accumulation in the adrenals; prevention of vascular congestion and accumulation of leukocytes in the liver; prevention of medullary congestion, hemorrhage and necrosis in the spleen; and fibrin thrombi deposition and edema formation in the lungs. LACI significantly attenuated leukocyte influx and vascular congestion in the lungs. The two baboons that received LACI at four hours and survived seven days showed a very similar prevention of pathological changes as those described above. However, there was some mild edema and fibrin present in alveolar sacs of the lungs with moderate leukocyte accumulation and vascular congestion. There was no evidence of multiple organ failure in any of the LACI treated baboons that survived seven days. This degree of protection is remarkable and unexpected given the delayed administration of LACI and the massive bacterial challenge afforded to the baboons.

The LACI-treated, *E. coli* challenged, 7 day survivors demonstrated a lower red blood cell concentration and an increase in leukocyte concentration. Histological examination did not reveal the occurrence of hemorrhage in any tissue. Thus the lower hematocrit may be attributed either to hemodilution or to the slow generation of erythrocytes in the bone marrow. LACI toxicology studies with uninfected baboons may be necessary to resolve this matter.

The decreased IL-6 levels observed in the *E. coli* challenged and LACI treated baboons in the present study show was unexpected and suggest that LACI either directly or indirectly exhibits an effect-on the inflammatory response. Thus, in addition to its anticoagulant activity, a physiologic role of LACI is useful in the modulation of the interaction of the coagulation pathway with various participants of the immune system.

TABLE 5

Weight, Sex, *E. coli* Dose and Survival Times of Control and LACI* Treated Baboons at +30 min**

| | Weight (kg) | Sex | Mean Dose *E. coli* (CFU/kg × 10$^{10}$) | Survival Time (hrs) |
|---|---|---|---|---|
| Control (*E. coli* + excipient control) | | | | |
| 26 | 12.1 | M | 5.71 | 46 |
| 27 | 9.8 | F | 5.60 | 52.5 |
| 32 | 6.4 | F | 5.23 | 9.7 |

TABLE 5-continued

Weight, Sex, E. coli Dose and Survival Times of Control and LACI* Treated Baboons at +30 min**

| | Weight (kg) | Sex | Mean Dose E. coli (CFU/kg × $10^{10}$) | Survival Time (hrs) |
|---|---|---|---|---|
| 37 | 7.7 | M | 5.26 | 30.5 |
| 41 | 5.9 | M | 5.70 | 60.5 |
| Mean (± SE) Experimental (E. coli + LACI) | 8.4 ± 1.1 | | 5.50 ± 0.11 | 39.9 ± 9.0 |
| 29 | 8.0 | M | 4.84 | >168 |
| 30 | 7.5 | M | 5.22 | >168 |
| 31 | 7.3 | M | 6.05 | >168 |
| 38 | 5.2 | M | 6.21 | >168 |
| 40 | 6.1 | M | 6.15 | >168 |
| Mean (± SE) | 6.8 ± 0.5 | | 5.69 ± 0.28 | 168 ± 0.0 |

*LACI - Tissue Factor Pathway Inhibitor
**LACI administered 30 min after the onset of a 2 hr infusion of E. coli

TABLE 6

Clinical Chemistry Summary of LACI Treated and Control Baboons at +30 min**

| | Control (Mean ± STD error) | | LACI [Mean ± STD error] | | |
|---|---|---|---|---|---|
| | T 0 | T + 12 hrs | T 0 | T + 12 hrs | +7 days |
| p < 0.05: | | | | | |
| Creat (mg/dL) | 0.64 ± 0.05 | 2.68 ± 0.27 | 0.64 ± 0.09 | 0.92 ± 0.07 | 0.48 ± .07 |
| T Bili (mg/dL) | 0.16 ± 0.02 | 1.35 ± 0.33 | 0.14 ± .02 | 0.30 ± 0.11 | 0.20 ± 0.05 |
| Uric Acid (mg/dL) | 0.38 ± 0.07 | 0.93 ± 0.18 | 0.50 ± 0.0 | 0.50 ± 0.00 | 0.32 ± 0.07 |
| Lactate (mEq/L) | 0.94 ± 0.38 | 6.05 ± 0.59 | 1.74 ± 0.47 | 4.10 ± 0.34 | 5.70 ± 1.21 |
| Triglycerides (mg/dL) | 64 ± 7 | 283 ± 19 | 101 ± 25 | 161 ± 28 | 130 ± 42 |
| Anion GAP (mEq/L) | 13.4 ± 0.75 | 19.25 ± 0.63 | 11.2 ± 1.24 | 11.25 ± .25 | 12.75 ± 1.03 |
| Cl (mEq/L) | 107.68 ± 3.73 | 109.58 ± 1.16 | 105.76 ± 0.52 | 117.62 ± 1.08 | 100.56 ± 6.61 |
| Na (mEq/L) | 150.58 ± 4.81 | 149.50 ± 0.65 | 146.04 ± 1.31 | 153.0 ± 1.0 | 142.26 ± 8.51 |
| p > 0.05 | | | | | |
| Alb (g/dL) | 3.82 ± 0.27 | 2.90 ± 0.33 | 3.66 ± 0.13 | 2.8 ± 0.06 | 2.68 ± 0.22 |
| Alk phosp. (IU/L) | 827 ± 59 | 949 ± 62 | 933 ± 68 | 1032 ± 121 | 937 ± 117 |
| AST (U/L) | 40 ± 3 | 1531 ± 783 | 45 ± 5 | 710 ± 484 | 68 ± 8 |
| BUN (mg/dL) | 19.4 ± 1.9 | 39.0 ± 4.1 | 29.6 ± 3.9 | 34.0 ± 3.2 | 13.8 ± 2.1 |
| CA (mg/dL) | 9.9 ± 0.4 | 7.1 ± 0.3 | 10.3 ± 0.2 | 7.9 ± 0.2 | 9.1 ± 0.5 |
| Chol (mg/dL) | 126 ± 10 | 94 ± 7 | 130 ± 3 | 86 ± 3 | 135 ± 16 |
| CK (U/L) | 604 ± 130 | 5979 ± 1705 | 795 ± 348 | 5594 ± 732 | 289 ± 79 |
| $CO_2$ (mEq/L) | 29.6 ± 2.0 | 20.4 ± 1.7 | 29.2 ± 0.9 | 23.7 ± 0.6 | 28.2 ± 1.9 |
| Cortisol (μg/dL) | 48.4 ± 7.9 | 120.2 ± 21.1 | 48.2 ± 12.2 | 110.5 ± 16.2 | 28.5 ± 2.6 |
| K (mEq/L) | 3.90 ± 0.14 | 4.75 ± 0.44 | 3.86 ± 0.14 | 4.32 ± 0.10 | 3.62 ± 0.25 |
| LDH (IU/L) | 311 ± 46 | 3956 ± 1112 | 317 ± 40 | 1819 ± 621 | 433 ± 58 |
| Phos (mg/dL) | 5.94 ± 0.69 | 8.28 ± 0.59 | 4.78 ± 0.34 | 7.66 ± 0.67 | 3.96 ± 0.55 |
| SGPT (IU/L) | 69 ± 23 | 936 ± 507 | 49 ± 9 | 366 ± 281 | 101 ± 11 |
| Total Protein (g/dL) | 7.00 ± 0.36 | 5.88 ± 0.35 | 6.62 ± 0.21 | 5.36 ± 0.18 | 5.92 ± 0.36 |

*LACI = Tissue Factor Pathway Inhibitor
**LACI administered 30 min after the onset of a 2 hr infusion of E. coli

TABLE 7

Individual Animal IL-6 Levels (ng/ml) LACI Administration at +30 min

| | T 0 | +30 | +120 | +240 | +360 | +720 |
|---|---|---|---|---|---|---|
| Control (E. coli + excipient control) | | | | | | |
| 26 | .034 | .027 | 21.5 | 102.3 | 347.2 | 468.5 |
| 27 | .018 | .047 | 27.6 | 58.4 | 88.7 | 31.1 |
| 32 | .010 | .020 | 35.6 | 217.6 | 321.7 | NT |

TABLE 7-continued

Individual Animal IL-6 Levels (ng/ml) LACI Administration at +30 min

| | T 0 | +30 | +120 | +240 | +360 | +720 |
|---|---|---|---|---|---|---|
| 37 | .038 | .048 | 36.7 | 97.6 | 196.9 | 183.2 |
| 41 | .028 | .052 | 32.3 | 101.7 | 100.4 | 63.4 |
| Mean ± SE | .03 ± .01 | .04 ± .01 | 30.7 ± 2.8 | 116 ± 26.8 | 211 ± 57.5 | 187 ± 63.4 |
| Experimental (*E. coli* + LACI) | | | | | | |
| 29 | NT | NT | 30.0 | 57.3 | 50.8 | 12.5 |
| 30 | .150 | .639 | 64.2 | 51.1 | 26.1 | 7.1 |
| 31 | .013 | .030 | 31.8 | 48.0 | 36.7 | 10.7 |
| 38 | .034 | .049 | 16.5 | 42.7 | 30.6 | 6.4 |
| 40 | .059 | .058 | 17.3 | 24.8 | 23.7 | 11.3 |
| Mean ± SE | .06 ± .03 | .19 ± .129 | 32.0 ± 8.7 | 44.8 ± 5.5 | 33.6 ± 4.8 | 9.6 ± 1.2 |

NT = Not Tested

TABLE 8

Weight, Sex, *E. coli* Dose and Survival Times of Control and LACI* Treated Baboons at +240 min**

| | Weight (kg) | Sex | Mean Dose *E. coli* (CFU/kg × 10¹⁰) | Survival Time (hrs) |
|---|---|---|---|---|
| Control (*E. coli* + excipient control) | | | | |
| 33 | 6.8 | M | 6.22 | 63.5 |
| 45 | 7.7 | F | 6.29 | 18.0 |
| 46 | 9.1 | M | 4.94 | 32.5 |
| 47 | 6.6 | M | 5.26 | 9.0 |
| 48 | 7.1 | M | 5.70 | 18.0 |
| Mean (± SE) | 7.5 ± 0.5 | | 5.68 ± .26 | 28.2 ± 9.6 |
| Experimental (*E. coli* + LACI) | | | | |
| 34 | 5.2 | M | 5.65 | 58 |
| 35 | 7.3 | M | 5.62 | >168 |
| 36 | 6.8 | M | 4.84 | >168 |
| 44 | 9.1 | M | 5.87 | 69 |
| 49 | 7.5 | F | 5.17 | 35 |
| Mean (± SE) | 7.2 ± 0.6 | | 5.43 ± 0.19 | 99.6 ± 28.5 |

*LACI = Tissue Factor Pathway Inhibitor
**240 min after the onset of a 2 hr infusion of *E. coli*

The present invention has been described with reference to specific embodiments. However, this application is intended to cover those changes and substitutions which may be made by those skilled in the art without departing from the spirit and the scope of the appended claims.

We claim:

1. A method for treating inflammation comprising administering to a patient a therapeutically effective amount of a protein selected from the group consisting of mature TFPI (SEQ ID NO: 5), ala-TFPI, ala-TFPI-1-160, ala-TFPI-13-161, and ala-TFPI-22-150, thereby treating the inflammation.

2. A method in accordance with claim 1, wherein the protein is chemically conjugated to a polymer consisting essentially of PEG or POG.

3. A method in accordance with claim 1, wherein the protein is administered at a dose between 1 μg/kg to 20 mg/kg.

4. A method in accordance with claim 1, wherein the protein is administered at a dose between 20 μg/kg to 10 mg/kg.

5. A method in accordance with claim 1, wherein the protein is administered at a dose between 1 to 7 mg/kg.

6. A method in accordance with claim 1 wherein the inflammation is chronic inflammation.

7. The method of claim 1 wherein the protein is ala-TFPI.

\* \* \* \* \*

SEQUENCE LISTING

```
<160> NUMBER OF SEQ ID NOS: 5

<210> SEQ ID NO 1
<211> LENGTH: 74
<212> TYPE: DNA
<213> ORGANISM: Homo sapiens

<400> SEQUENCE: 1
catggctgat tctgaagaag atgaagaaca tactacgact aagacttctt ctacttcttg     60
tatgataata gtga                                                       74

<210> SEQ ID NO 2
<211> LENGTH: 68
<212> TYPE: DNA
<213> ORGANISM: Homo sapiens

<400> SEQUENCE: 2
ttatcactga tactgaactg ccaccgctga aactgatgca ctatgacttg acggtggcga     60
ctttgact                                                              68

<210> SEQ ID NO 3
<211> LENGTH: 21
```

```
<212> TYPE: DNA
<213> ORGANISM: Homo sapiens

<400> SEQUENCE: 3
ataacaaagc ttacatattt t                                              21

<210> SEQ ID NO 4
<211> LENGTH: 20
<212> TYPE: DNA
<213> ORGANISM: Homo sapiens

<400> SEQUENCE: 4
atatatccat ggctgattct                                                20

<210> SEQ ID NO 5
<211> LENGTH: 276
<212> TYPE: PRT
<213> ORGANISM: Homo sapiens

<400> SEQUENCE: 5
```

Asp Ser Glu Glu Asp Glu His Thr Ile Ile Thr Asp Thr Glu Leu
 1               5                  10                  15

Pro Pro Leu Lys Leu Met His Ser Phe Cys Ala Phe Lys Ala Asp
            20                  25                  30

Gly Pro Cys Lys Ala Ile Met Lys Arg Phe Phe Phe Asn Ile Phe
        35                  40                  45

Arg Gln Cys Glu Glu Phe Ile Tyr Gly Gly Cys Glu Gly Asn Gln Asn
    50                  55                  60

Arg Phe Glu Ser Leu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
        275